(12) United States Patent
Petersen-Mahrt et al.

(10) Patent No.: US 7,820,442 B2
(45) Date of Patent: Oct. 26, 2010

(54) ACTIVATION INDUCED DEAMINASE (AID)

(75) Inventors: Svend K. Petersen-Mahrt, Cambridge (GB); Reuben Harris, Cambridge (GB); Michael Samuel Neuberger, Cambridge (GB); Rupert Christopher Landsdowne Beale, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 10/985,321

(22) Filed: Nov. 10, 2004

(65) Prior Publication Data

US 2006/0019262 A1    Jan. 26, 2006

Related U.S. Application Data

(63) Continuation of application No. PCT/GB03/02002, filed on May 9, 2003.

(30) Foreign Application Priority Data

| May 10, 2002 | (GB) | ............................... | 0210755.5 |
| Jun. 14, 2002 | (GB) | ............................... | 0213751.1 |
| Jul. 29, 2002 | (GB) | ............................... | 0217519.8 |

(51) Int. Cl.

| C12N 15/87 | (2006.01) |
| C12N 15/00 | (2006.01) |
| G01N 33/554 | (2006.01) |
| G01N 33/569 | (2006.01) |
| C12P 1/00 | (2006.01) |
| C12P 39/00 | (2006.01) |
| C12P 21/06 | (2006.01) |
| C12P 21/04 | (2006.01) |
| C07H 21/02 | (2006.01) |
| C07H 21/04 | (2006.01) |

(52) U.S. Cl. ..................... 435/463; 435/7.32; 435/41; 435/42; 435/69.1; 435/69.7; 435/440; 536/23.1; 536/23.2; 536/23.4

(58) Field of Classification Search .................... 435/6, 435/7.1, 325, 326, 455, 7.32, 41, 42, 69.1, 435/69.7, 440, 463; 536/23.1, 23.2, 23.4

See application file for complete search history.

(56) References Cited

U.S. PATENT DOCUMENTS

| 2005/0054073 A1* | 3/2005 | Honjo et al. | ................. | 435/232 |
| 2005/0095712 A1* | 5/2005 | Martin et al. | ............... | 435/455 |

FOREIGN PATENT DOCUMENTS

| AU | 716 748 B | 10/1996 |
| EP | 1 174 509 A1 | 1/2002 |
| WO | WO 03/061363 | 7/2003 |

OTHER PUBLICATIONS

Siddiqui et al. Exp. Cell Research, 252: 154-164, 1999.*

Yamanaka et al., Apolipoprotein B mRNA-editing protein induces hepatocellular carcinoma and dysplasia in transgenic animals, *Proc. Natl. Acad. Sci. USA, Biochemisty*, Aug. 1995, vol. 92, pp. 8483-8487.

International Search Report Related To PCT/GB 03/02002.

Martin A. et al., Activation-Induced Cytidine Deaminase Turns On Somatic Hypermutation In Hybridomas, *Nature*, vol. 415, Feb. 24, 2002, pp. 802-806.

Jarmuz A. et al., An Anthropoid-Specific Locus Of Orphan C To U RNA-Editing Enzymes On Chromosome-22, *Genomics*, vol. 79, No. 3, Mar. 2002, pp. 285-296.

Manis JP., Mechanism And Control Of Class-Switch Recombination, *Trends in Immunology*, Elsevier, Cambridge, GB, vol. 23, No. 1, Jan. 1, 2002, pp. 31-39.

MacGinnitie A.J. et al., Mutagenesis Of Apobec-1, The Catalytic Subunit Of The Mammalian Apolipoprotein B mRNA Editing Enzyme, Reveals Distinct Domains That Meiate Cytosine Nucleoside Deaminase, RNA Binding, and RNA Editing Activity, *The Journal of Biological Chemistry*, vol. 270, No. 24, Jun. 16, 1995, pp. 14768-14775.

Okazaki IM. et al., The Aid Enzyme Induces Class Switch Recombination In Fibroblasts, *Nature*, vol. 416, Mar. 21, 2002, pp. 340-345.

Yelamos J., et al., Targeting of Non-IG Sequences In Place Of The V Segment By Somatic Hypermutation, *Nature*, MacMillan Journals Ltd. London, GB, vol. 376, No. 6537, 1995, pp. 225-229.

Harris RS, Petersen-Mahrt SK. et al., RNA Editing Enzyme APOBEC1 And Some Of Its Homologs Can Act As DNA Mutators, *Molecular Cell*, vol. 10, No. 2002, pp. 1247-1253.

Petersen-Mahrt SK. et al., Aid Mutates *E. coli* suggesting a DNA Deamination Mechanism for Antibody Diversification, *Nature*, vol. 418, Jul. 4, 2002, pp. 99-103.

Yoshikawa, K. et al., "AID Enzyme-Induced Hypermutation in an Actively Transcribed Gene in Fibroblasts," Science 296:2033-2036 (2002).

Conticello, S.G. et al., "Evolution of the AID/APOBEC Family of Polynucleotide (Deoxy)cytidine Deaminases," Molecular Biology and Evolution 22(2):367-377 (2005).

Cumbers, S.J. et al., "Generation and iterative affinity maturation of antibodies in vitro using hypermutating B-cell lines," Nature Biotech. 20:1129-1134 (2002).

Storb, U. et al., "Somatic hypermutation of immunoglobulin and non-immunoglobulin genes," Phil. Trans. R. Soc. Lond. B 356:13-19 (2001).

Wang, L. et al., "Evolution of new nonantibody proteins via iterative somatic hypermutation," PNAS USA 101(48):16745-16749 (2004).

Kawai et al., "Isolation and Analysis of Lipase-Overproducing Mutants of *Serratia marcescens*," Journal of Bioscience and Bioengineering, 91(4): 409-415 (2001).

Stefan et al., "Directed Evolution of β-Galactosidase from *Escherichia coli* by Mutator Strains Defective in the 3'-5' Exonuclease Activity of DNA polymerase III," *FEBS Letters*, 493: 139-143 (2001).

(Continued)

*Primary Examiner*—Thaian N Ton
(74) *Attorney, Agent, or Firm*—Leydig, Voit & Mayer, Ltd.

(57) ABSTRACT

The present invention identifies that the expression of Activation Induced Deaminase (AID) or its homologues in cells confers a mutator phenotype and thus provides a method for generating diversity in a gene or gene product as well as cell lines capable of generating diversity in defined gene products. The invention also provides methods of modulating a mutator phenotype by modulating AID expression or activity.

22 Claims, 15 Drawing Sheets

OTHER PUBLICATIONS

Harris et al., AID is essential for Immunoglobulin V. Gene Conversion in a Cultured B Cell Line, *Current Biology*, 12(5): 435-438 (Mar. 5, 2002).

Martin et al., "Somatic Hypermutation of the AID Transgene in B and Non-B Cells," *PNAS*, 99(9): 12304-12308 (2002).

Muramatsu et al., "Specific Expression of Activation-Induced Cytidine Deaminase (AID), a Novel Member of the Rna-Editing Deaminase Family in Germinal Center B Cells," *J. Biol. Chem.*, 274: 18470-18476 (1999).

Nagaoka et al., "Activation-Induced Deaminase (AID)-Directed Hypermutation in the Immunoglobuling Sµ Region: Implication of AID Involvement in a Common Step of Class Switch Recombination and Somatic Hypermutation," *J. Exp. Med.*, 195: 529-534 (Feb. 2002).

Peterson-Mahrt et al., In Vitro Deamination of Cytosine to Uracil in Single-Stranded DNA by Apolipoprotein B Editing Complex Catalytic Subunit 1 (APOBEC1), *The Journal of Biological Chemistry*, 278(22): 19583-19586 (May 30, 2003).

Pham et al., "Processive AID-catalysed cytosine deamination on single-stranded DNA simulates somatic hypermutation," *Nature*, 424(3): 103-107 (Jul. 2003).

Rada et al., "Hot Spot Focusing of Somatic Hypermutation in MSH2-Deficient Mice Suggests Two Stages of Mutational Targeting," *Immunity*, 9(1): 135-141 (Jul. 1998).

* cited by examiner

Figure 3 a

Vector
n=122

```
                            ggggg
                            ggggg
                            gggg
          ggg    tt         aaggg                              tttt
          gg     tt         ttt                                tttt
          a      t          tt                  tt             ttt
          a      ca    t    tt                  t              g  gt
      agc cag ctg tct cag ttt atg gac cag aac aac ccg ctg tct gag att acg gac aaa cgt cgt atc
          1530                        1560                                         1590
 tt
 tt      a
 t       c    t                                                              a
 tcc gca ctc ggc cca ggc ggt ctg acc cgt gaa cgt gca ggc ttc gaa gtt cga gac gta cac ccg
                       1620                                         1650
                                                                       ccccgggg
                                                                       ccccggg
                                                                       ccccgg
                                                                       cccgg
                           t   tt                                      ccgg
                          a at  t                    a                 tag     t
 act cac tac ggt cgc gta tgt cca atc gaa acc cct gaa ggt ccg aac atc ggt ctg atc aac tct
                  1680                                         1710
```

APOBEC1
n=136

```
                    ttt
                    tttt
                    ttttt
                    tttttt                                   ttt
                    ttttttt              a                   ttt
                    tttttt              aaaa                 ttt
                    ttttt               aaaa                 tt
                    ttt                                      t
      agc cag ctg tct cag ttt atg gac cag aac aac ccg ctg tct gag att acg gac aaa cgt cgt atc
          1530                        1560                                         1590
tttttt
tttttttt
tttttttt
tttttttt
ttttttt
t
 tcc gca ctc ggc cca ggc ggt ctg acc cgt gaa cgt gca ggc ttc gaa gtt cga gac gta cac ccg
                       1620                                         1650
                                           t
                                           t
 act cac tac ggt cgc gta tgt cca atc gaa acc cct gaa ggt ccg aac atc ggt ctg atc aac tct
                  1680                                         1710
``` b

Vector

| From\To | A | C | G | T |
|---|---|---|---|---|
| A | | 13 | 16 | 10 |
| C | 4 | | 4 | 25 |
| G | 2 | | | 3 |
| T | 3 | 4 | 16 | |

27% Transition at dC/dG

APOBEC1

| From\To | A | C | G | T |
|---|---|---|---|---|
| A | | | | |
| C | | | | 92 |
| G | 8 | | | |
| T | | | | |

100% Transition at dC/dG

Figure 6

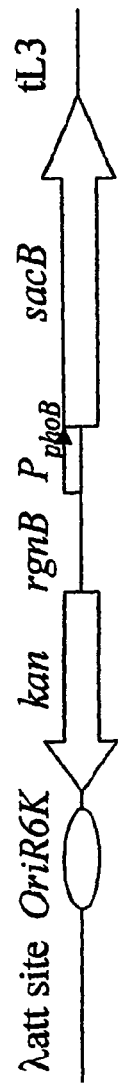
Figure 8a
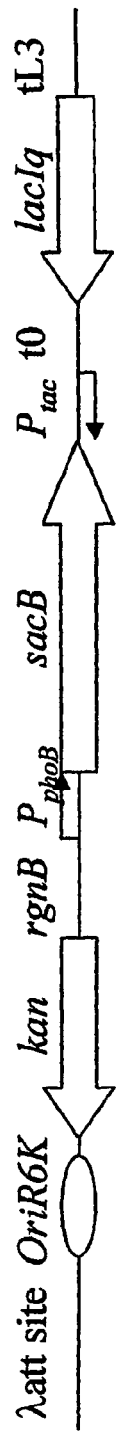
Figure 8b
| | Point Mutations (Transitions at C or G) | Insertion elements |
|---|---|---|
| Spontaneous | 3 (2) | 13 |
| APOBEC-1 | 33 (32) | 4 |
Figure 9

| | Integrated Target | Expression Plasmid | Growth medium | Median Mutation Frequecy | Frequency/ Vector |
|---|---|---|---|---|---|
| A | pRB700 | pTrc99a | LB | $2.0 \times 10^{-6}$ | |
| B | pRB740 | pTrc99a | LB | $1.9 \times 10^{-6}$ | |
| C | pRB700 | pTrc99a | MOPS + 0.1mM Pi | $1.0 \times 10^{-6}$ | |
| D | pRB740 | pTrc99a | MOPS + 0.1mM Pi | $9.7 \times 10^{-7}$ | |
| E | pRB700 | pRH200 | LB | $2.3 \times 10^{-5}$ | 12 fold |
| F | pRB740 | pRH200 | LB | $3.6 \times 10^{-5}$ | 19 fold |
| G | pRB700 | pRH200 | MOPS + 0.1mM Pi | $8.5 \times 10^{-6}$ | 9 fold |
| H | pRB740 | pRH200 | MOPS + 0.1mM Pi | $2.9 \times 10^{-2}$ | 30000 fold |
| I | pRB740 | pRH200 | MOPS + 0.1mM Pi | $4.3 \times 10^{-2}$ | 44000 fold |

| | Expected size PCR / Total PCR products | |
|---|---|---|
| | Uninduced | Bidirectional Induction |
| AID | 2/10 | 10/10 |
| APOBEC3G | 5/10 | 7/10 |

| | Transitions at C or G / Total mutations | |
|---|---|---|
| | Uninduced | Bidirectional Induction |
| AID | 1/10 | 8/10 |
| APOBEC3G | 2/10 | 5/10 |

| | Transitions at C or G / Total point mutations | |
|---|---|---|
| | Uninduced | Bidirectional Induction |
| AID | 1/1 | 8/8 |
| APOBEC3G | 2/3 | 5/5 |

| | Median Mutation Frequency / Background | |
|---|---|---|
| | Uninduced | Bidirectional Induction |
| AID | 1.7 | 3.3 |
| APOBEC3G | 1.8 | 2.4 |

ACTIVATION INDUCED DEAMINASE (AID)

RELATED APPLICATIONS

This application is a continuation of International Application No. PCT/GB03/02002, filed May 9, 2003, which designates the United States and was published in English and which claims priority to foreign application no. GB 0210755.5, filed May 10, 2002, foreign application no. GB 0213751.1, filed Jun. 14, 2002 and foreign application no. GB 0217519.8, filed Jul. 29, 2002, the entirety of which is incorporated herein by reference.

The present invention identifies that the expression of Activation Induced Deaminase (AID) and its homologues, such as Apobec, in cells confers a mutator phenotype and thus provides a method for generating diversity in a gene or gene product as well as cell lines capable of generating diversity in defined gene products. The invention also provides methods of modulating a mutator phenotype by modulating the expression or activity of AID or its homologues.

BACKGROUND

In normal cells, a low mutation rate ensures genetic stability and this depends on effective DNA repair mechanisms for repairing the many accidental changes that occur continually in DNA.

However, during the generation of antibodies, point mutations occur within the V-region coding sequence of the antigen receptor loci and the rate of mutation observed, called somatic hypermutation, is about a million times greater than the spontaneous mutation rate in other genes. The antigen receptor loci are the only loci in human cells that undergo programmed genetic alterations. However, the mechanisms that allow the nucleotide changes to be controlled and targeted to the DNA of a precisely specified part of the genome in this way is not known.

Functional antigen receptors are assembled by RAG-mediated gene rearrangement and the isotype switch from IgM to IgG, IgA and IgE is effected by class switch recombination. Aberrant forms of RAG-mediated gene rearrangement and class switch recombination have been shown to underpin many of the chromosomal translocations associated with lymphoid malignancies. In the case of somatic hypermutation, it was proposed several years ago by Rabbitts et al (1984 Nature 309, 592-597) that the chromosomal translocations which bring the c-myc proto-oncogene into the vicinity of the IgH locus could make it a substrate for the antibody hypermutation mechanism. Recent evidence using hypermutating cell lines has provided evidence in support of this (Bemark, M and Neuberger, M. S. 2000 Oncogene 19, 3404-3410). A wider role for aberrant hypermutation came with the finding that several genes apart from the immunoglobulin V genes can (without being translocated into the Ig loci) apparently act as substrates for the antibody hypermutation mechanism in that they exhibit an increased frequency of point mutation in hypermutating B cells. Recent evidence also points to a high frequency of mutations in many B cell tumours and it has been proposed that this is a result of a transient hypermutation phase caused by the antibody hypermutation mechanism. In all these cases, the aberrant mutations are largely at dC/dG residues.

An uncontrolled and enhanced rate of mutation in non-antibody producing cells can also be deleterious. For example, mutations are the hallmark of cancer and the enhanced rate of mutation in cancer cells may explain their capability to continually grow and evade the normal human defenses. The "mutator phenotype" hypothesis attributes this phenomenon to an increasing rate of errors in DNA replication as a tumour grows. According to this theory, genes encoding proteins normally interacting with nucleotides such as DNA polymerases and DNA repair enzymes may be faulty in cancer cells and therefore cause subsequent mutations.

In vitro, understanding and harnessing the means for controlling an enhanced rate of mutation can be usefully employed, for example, in generating diversity of gene products such as generating antibody diversity.

Many in vitro approaches to the generation of diversity in gene products rely on the generation of a very large number of mutants which are then selected using powerful selection technologies. For example, phage display technology has been highly successful as providing a vehicle that allows for the selection of a displayed protein (Smith, G. P. 1985 Science, 228, 1315-7; Bass et al. *Proteins.* 8, 309-314, 1990; McCafferty et al., 1990 Nature, 348, 552-4; for review see Clackson and Wells, 1994 Trends Biotechnol. 12, 173-84). Similarly, specific peptide ligands have been selected for binding to receptors by affinity selection using large libraries of peptides linked to the C terminus of the lac repressor Lac1 (Cull et al., 1992 Proc Natl Acad Sci USA, 89, 1865-9). When expressed in *E. coli* the repressor protein physically links the ligand to the encoding plasmid by binding to a lac operator sequence on the plasmid. Moreover, an entirely in vitro polysome display system has also been reported (Mattheakis et al., 1994 Proc Natl Acad Sci USA, 91, 9022-6) in which nascent peptides are physically attached via the ribosome to the RNA which encodes them.

Artificial selection systems to date rely heavily on initial mutation and selection, similar in concept to the initial phase DNA rearrangement involving the joining of immunoglobulin V, D and J gene segments which occurs in natural antibody production, in that it results in the generation of a "fixed" repertoire of gene product mutants from which gene products having the desired activity may be selected.

Unlike in the natural immune system, however, artificial selection systems are poorly suited to any facile form of "affinity maturation", or cyclical steps of repertoire generation and development. One of the reasons for this is that it is difficult to generate enough mutations and to target these to regions of the molecule where they are required, so subsequent cycles of mutation and selection do not lead to the isolation of molecules with improved activity with sufficient efficiency.

In vivo, after the primary repertoire of antibody specificities is created by V-D-J rearrangement, and following antigen encounter in mouse and man, the rearranged V genes in those B cells that have been triggered by the antigen are subjected to two further types of genetic modification. Class switch recombination, a region-specific but largely non-homologous recombination process, leads to an isotype change in the constant region of the expressed antibody. Somatic hypermutation introduces multiple single nucleotide substitutions in and around the rearranged V gene segments. This hypermutation generates the secondary repertoire from which good binding specificities can be selected thereby allowing affinity maturation of the humoral immune response. In chicken and rabbits (but not man or mouse) an additional mechanism, gene conversion, is a major contributor to V gene diversification.

Much of what is known about the somatic hypermutation process which occurs during affinity maturation in natural antibody production has been derived from an analysis of the mutations that have occurred during hypermutation in vivo (for reviews see Neuberger and Milstein, 1995 Curr. Opin.

Immunol. 7, 248-254; Weill and Reynaud, 1996 *Immunol Today* 17, 92-97; Parham, 1998 Immunological Reviews, Vol. 162 (Copenhagen, Denmark: Munksgaard)). Most of these mutations are single nucleotide substitutions which are introduced in a stepwise manner. They are scattered over the rearranged V domain, though with characteristic hotspots, and the substitutions exhibit a bias for base transitions. The mutations largely accumulate during B cell expansion in germinal centres (rather than during other stages of B cell differentiation and proliferation) with the rate of incorporation of nucleotide substitutions into the V gene during the hypermutation phase estimated at between $10^{-4}$ and $10^{-3}$ $bp^{-1}$ $generation^{-1}$ (McKean et al., 1984; Berek & Milstein, 1988). However, a greater understanding of the steps involved in these later stages of hypermutation would enable a more diverse range of gene products to be obtained.

All three of the above processes, somatic hypermutation, gene conversion and class-switch recombination, have been shown to depend upon activity of the protein Activation Induced Deaminase (AID) (Muramatsu et al. (1999); Muramatsu M. et al. (2000); Revy, P. et al. (2000); Arakawa, H. et al. (2002); Harris, R. S. et al. (2002); Martin, A et al. (2002) and Okazaki, L et al. (2002)) which has been suggested (by virtue of its homology with Apobec-1 (Muramatsu et al. (1999)) to act by RNA editing. However, evidence that the three processes could be initiated by a common type of DNA lesion (Maizels et al. (1995); Weill et al. (1996); Sale et al. (2001); Ehrenstein et al. (1999)) taken with the fact that first phase of hypermutation targets dG/dC (Martin et al. (2002); Rada et al. (1998); Wiesendanger et al. (2000)) has suggested that AID may act directly on dG/dC pairs in the immunoglobulin locus. However, to date, the actual function of AID has not been described.

The AID homologue Apobec-1 has been identified as playing a role in modifying RNA. Apobec-1 is a catalytic component of the apolipoprotein B (apoB) RNA editing complex that performs the deamination of $C_{6666}$ to U in intestinal apoB RNA thereby generating a premature stop codon. Indeed, the oncogenic activity of Apobec-1, identified by its overexpression in transgenic mice, has previously been attributed to its RNA editing activity acting on inappropriate substrates.

Deamination of cytosine to uracil can occur in vivo at the level of nucleotide and in DNA as well as RNA. In the context of DNA, the low level deamination of cytosine to uracil which takes place spontaneously (and which might be of relatively minor significance when it occurs with free nucleotides or in mRNA) can have major effects, contributing to genome mutation, cancer and evolution (Lindahl, T. (1993) Nature 362, 709-715). However, to date, there is no biochemical evidence that APOBEC family members can trigger such deamination in vitro.

SUMMARY OF THE INVENTION

The present inventors have demonstrated that expression of AID in *Escherichia coli* gives a mutator phenotype yielding DNA nucleotide transitions at dG/dC. The mutation frequency is enhanced by deficiency in uracil-DNA glycosylase indicating that AID acts by deaminating dC residues in DNA.

In addition, the expression of AID homologues, Apobec-1, Apobec3C and Apobec3G, including their expression as part of a fusion protein in *E. coli* also yields a mutator phenotype and these homologues show an increased potency of mutator activity on DNA sequences when compared to AID.

Furthermore, deamination of cytosine to uracil in DNA can be achieved in vitro using partially purified APOBEC1 from extracts of transformed *Escherichia coli*. Its activity on DNA is specific for single-stranded DNA and exhibits dependence on local sequence context.

Accordingly, in a first aspect of the invention there is provided a cell modified to express AID, or an AID variant, derivative or homologue, and having a mutator phenotype. Suitably, the cell is modified to stably express AID, or an AID variant, derivative or homologue, and having a mutator phenotype.

By "stable expression" of a gene is meant that the gene and its expression is substantially maintained in successive generations of cells derived from transfected cells. In particular, the term "stable expression" is not intended to encompass the transient expression of a protein in a bacterial cell for the purpose of protein purification.

In another embodiment, the cell is transiently transfected to express AID, or an AID variant, derivative or homologue, and having a mutator phenotype.

As used herein, "mutator phenotype" means an increased mutation frequency in the transfected cells modified to express AID or its homologues when compared to non-modified, non-transfected cells. Methods for measuring mutation frequency are described herein. Suitably the mutations are nucleotide transitions at dG/dC as a result of deamination of dC residues in DNA. The term "mutator activity" refers to the activity that confers the mutator phenotype.

In one embodiment, said cell is a prokaryotic cell, such as bacteria. Suitable bacteria include *E. coli*.

In another embodiment, the cell is a modified eukaryotic cell in which altered AID expression has been induced by introduction of AID gene with the proviso that said eukaryotic cell is not a cell of the human B lymphocyte lineage and, in particular, is not a human Ramos, BL-2 or CL-01 cell nor a cell derived from the chicken cell line, DT40. Suitably said cell is derived from mouse or man and is capable of generating immunoglobulin diversity through somatic hypermutation or class switching.

In another embodiment, the AID homologue is Apobec and is, in particular, selected from Apobec family members such as Apobec-1, Apobec3C or Apobec3G (described, for example, by Jarmuz et al (2002)).

In yet another embodiment, the AID variant is a fusion protein. Suitably, said fusion protein is AID, Apobec-1, Apobec3C or Apobec3G in which a heterologous protein or peptide domain has been fused at either its N- or C-terminus. Preferably, the heterologous peptide is fused at the amino terminus. Suitably, said heterologous peptide domain is a binding domain which is one half of a specific binding pair which can interact with the second half of said pair to form a complex. Suitable binding pairs include two complementary components which can bind in a specific binding reaction. Examples of specific binding pairs include His-tag-Nickel, DNA binding domain-DNA binding domain recognition sequence, antibody-antigen, Biotin-Streptavidin etc.

The data presented herein are consistent with AID or its homologues activating deamination of dC as an enhancement of the effect is observed in cells lacking uracil-DNA glycosylase (UDG).

Accordingly, in another embodiment, said cell further comprises a genetic background which confers an enhanced mutator phenotype effect in a particularly preferred embodiment, the genetic background of a prokaryotic cell confers a UDG deficiency on the cell. Said UDG deficiency is preferably induced by interfering with UDG expression such as, for example, creating a ung- background. In some *E. Coli* ung-1 mutants, some back up UDG activity is provided by the product of the mug gene. Thus, in a further embodiment, the cell comprises a combined background of ung- and mug-.

The introduction of modified expression of AID or an AID homologue into a cell can increase the mutation rate above the background mutation rate that would normally be observed in that cell. Suitably, the modified cell is capable of generating mutations in a defined gene product. This can be particularly useful in the generation of gene diversity or example in the generation of antibody diversity where the defined gene product is an immunoglobulin V region gene.

Such cells according to any embodiment of the first aspect and displaying an enhanced rate of mutation can be useful in a method for preparing a gene product having a desired activity.

Preferably the gene product which is desired to mutate is provided to AID or its homologues as single-stranded DNA. Single stranded DNA may be provided by introducing single stranded DNA directly or by introducing double stranded DNA which is later converted to single stranded, for example, through enzymatic action such as helicase or transcriptase activity.

In another aspect of the invention, there is provided a fusion protein comprising an AID, or AID variant, derivative or homologue, polypeptide having a mutator phenotype operably linked to one half of a specific binding pair.

The term "operably linked" refers to a juxtaposition wherein the components described are in a relationship permitting them to function in their intended manner. For example, an AID polypeptide "operably linked" to one half of a specific binding pair is linked through ligation of the nucleic acid coding sequences or otherwise such that a fusion protein is produced in which the mutator activity of AID is unimpaired whilst allowing the specific binding pair to form through interaction of the said one half with its complement.

In a preferred embodiment, the one half of the specific binding pair in said fusion protein is a DNA binding domain.

Preferably, the AID homologue is one of the Apobec family of proteins and, suitably, is selected from the group consisting of Apobec-1, Apobec3G and Apobec-3C.

In another aspect of the invention, there is provided a vector for expressing a fusion protein in accordance with the previous aspect.

In yet another aspect of the invention, there is provided a cell modified to express a fusion protein in accordance with that aspect of the invention.

The mutator activity of AID can be harnessed to drive mutation of specific gene products of interest. Accordingly, in a further aspect of the invention there is provided a method for preparing a gene product having a desired activity, comprising the steps of:
a) expressing a nucleic acid encoding the gene product in a population of cells according to the invention;
b) identifying a cell or cells within the population of cells which expresses a mutant gene product having the desired activity, and
c) establishing one or more clonal populations of cells from the cell or cells identified in step (b), and selecting from said clonal populations a cell or cells which expresses a gene product having an improved desired activity.

In one embodiment, the nucleic acid encoding the gene product is available to AID or an AID homologue as single-stranded DNA.

Suitably, the nucleic acid encoding the gene product is operably linked to one component of a specific binding pair. In this embodiment, a nucleic acid operably linked to the one component, or second half, of a specific binding pair is ligated in such a way that the binding of the other component, or first half, of a specific binding pair can take place. Thus, where the first half of specific binding pair is linked in a fusion protein to the AID polypeptide having mutator activity, binding of the first and second halves of the specific binding pairs brings the mutator protein into range with the nucleic acid sequence such that directed mutation of that particular nucleic acid sequence can take place.

In a particularly preferred embodiment, the specific binding pair is a DNA binding protein-DNA binding protein recognition sequence. In this embodiment, the population of cells comprises cells expressing a fusion protein being a fusion of AID polypeptide to a DNA binding protein (or DNA binding domain) and the nucleic acid sequence encoding the gene product is operably linked to the DNA binding protein recognition sequence. This would allow the mutator activity of AID or its homologues to be specifically directed to the nucleic acid encoding the gene product of interest.

Accordingly, in another aspect of the invention, there is provided a method for directing mutation to a specific gene product of interest. Suitably said method comprises the steps of:
i) generating a nucleic acid construct comprising a nucleic acid sequence encoding a gene product operably linked to a DNA binding protein recognition sequence;
ii) transfecting said nucleic acid construct into a population of host cells expressing a fusion protein in accordance with the invention;
iii) incubating said transfected host cells under conditions suitable for allowing the specific binding pairing of DNA binding protein to DNA binding protein recognition sequence to occur, and
iv) identifying a cell or cells within the population of cells which expresses a mutant gene product having the desired activity; and
v) establishing one or more clonal populations of cells from the cell or cells identified in step (iv), and selecting from said clonal populations a cell or cells which expresses a gene product having an improved desired activity.

Suitably said host cells may be prokaryotic, bacterial cells such as *E. Coli* or they may be eukaryotic cells such as yeast or mammalian cells.

In one embodiment, the population of cells in accordance with the invention is derived from a clonal or polyclonal population of cells which comprises cells capable of constitutive hypermutation of V region genes.

The gene product may be an endogenous gene product such as the endogenous immunoglobulin polypeptide, a gene product expressed by a manipulated endogenous gene or a gene product expressed by a heterologous transcription unit operatively linked to control sequences which direct somatic hypermutation, as described former below. In this embodiment, the gene product is operably linked to a nucleic acid which directs hypermutation.

Alternatively, the gene product may be a heterologous gene product.

The nucleic acid which is expressed in the cells of the invention and subjected to hypermutation may be an endogenous region, such as the endogenous V region, or a heterologous region inserted into the cell line of the invention. This may take the form, for example, of a replacement of the endogenous V region with heterologous transcription unit(s), such as a heterologous V region, retaining the endogenous control sequences which direct hypermutation; or of the insertion into the cell of a heterologous transcription unit under the control of its own control sequences to direct hypermutation, wherein the transcription unit may encode V region genes or any other desired gene product. The nucleic acid according to the invention is described in more detail below.

In another embodiment the gene product may be an endogenous gene product which is not normally subject to hypermutation. Suitable gene products include genes implicated in disease, oncogenes and other target genes. Thus, the gene product may be any gene product in which mutation is desirable.

In one embodiment, the endogenous or heterologous gene may be integrated into a chromosome.

In step b) or step (iv) above, the cells are screened for the desired gene product activity. This may be, for example in the case of immunoglobulins, a binding activity. Other activities may also be assessed, such as enzymatic activities or the like, using appropriate assay procedures. Where the gene product is displayed on the surface of the cell, cells which produce the desired activity may be isolated by detection of the activity on the cell surface, for example by fluorescence, or by immobilising the cell to a substrate via the surface gene product. Where the activity is secreted into the growth medium, or otherwise assessable only for the entire cell culture as opposed to in each individual cell, it is advantageous to establish a plurality of clonal populations from step a) in order to increase the probability of identifying a cell which secretes a gene product having the desired activity. Advantageously, the selection system employed does not affect the cell's ability to proliferate and mutate.

Preferably, at this stage (and in step c) or step v)) cells which express gene products having a better, improved or more desirable activity are selected. Such an activity is, for example, a higher affinity binding for a given ligand, or a more effective enzymatic activity. Thus, the method allows for selection of cells on the basis of a qualitative and/or quantitative assessment of the desired activity. Successive rounds of selection may allow for directed evolution in a gene product. Selection of mutants may also be achieved by growth or selection on selective media as described herein.

In a preferred embodiment, the "population of cells" in the method is a population of prokaryotic cells. In another embodiment, the "population of cells" is a population of yeast cells.

The targeted mutation of a specific gene product of interest can be enhanced by providing the nucleic acid encoding the gene product in a modified construct. Suitably the construct is arranged such to favour generation of a single-stranded substrate oligonucleotide (i.e. the nucleic acid encoding the gene product of interest). An increased availability of single stranded DNA can be achieved by providing the substrate oligonucleotide between two convergent promoters. In one embodiment, this construct favours the generation of single stranded DNA through DNA bending caused by promoter activity. In another embodiment, this construct favours single stranded DNA through bi-directional transcription activation.

Accordingly, in another aspect of the invention there is provided a construct for use in a method in accordance with the invention said construct comprising a nucleic acid encoding the gene product of interest wherein said nucleic acid is placed under the control of a first promoter upstream of the coding sequence and further comprising a second promoter downstream of the coding sequence in the opposite orientation. Such a construct may be referred to as a construct for convergent transcription.

A number of suitable promoter sequences are known to those skilled in the art. For example, suitable Prokaryotic promoters include Activators such as AraBAD, PhoA, Repressors such as Tet, Lac, Trp, Hybrid Lac/Trp such as Tac, pL and Regulatable hybrids of pL such as pL-tet or Viral Polymerase, such as T7. Suitable Eukaryotic promoters include, for example, RNA Polymerase I (e.g. 45S rDNA), RNA Polymerase II (e.g. Gal4, β-Actin, Viral promoters, such as CMV-IE and Artificial promoters including Tet-on, Tet-off) or RNA Polymerase III promoters including H1 RNA and U6 snRNA. In particular, promoters include the PhoB promoter and inducible promoters such as IPTG inducible Trc promoter. Suitably said construct is as described in the examples section herein.

In another aspect of the invention there is provided a method of identifying components of AID-dependant mutation activity comprising expressing AID in a cell deficient in a particular gene and assessing mutator activity compared to activity in a cell expressing said gene.

By "components of AID dependant mutation activity" is meant aspects or cellular components which contribute to the molecular role of AID (or its homologues) and includes proteins or nucleic acid components which interact with AID in its mutator function.

In a further aspect of the invention there is provided a method of screening for a modulator of AID activity comprising:
expressing AID in a prokaryotic cell;
maintaining the AID-expressing prokaryotic cell in the presence of a selectable medium;
detecting the presence of colonies in the absence or presence of a test compound wherein a modified number of colonies when compared to a sample in the absence of a test compound is indicative of the ability of the test compound to modify AID mutator activity.

By "AID activity" is meant activity of AID or any of its homologues.

Preferably, the modified number of colonies in the presence of the test compound is an increased number and is therefore indicative of enhanced AID-mediated mutation.

In another aspect of the invention there is provided a method of conferring a mutator phenotype on a cell comprising expressing AID or its homologues in a cell.

Modifying a cell to confer an increased frequency of mutations by introducing AID expression is equivalent to a method of introducing mutations into a cell comprising expressing AID, the mutator protein.

In another aspect of the invention, there is provided a use of AID or a functional homologue thereof in triggering mutation in a cell. In particular, there is provided a use of AID to introduce nucleotide transitions at dG/dC as a result of deamination of dC residues in DNA.

There are several members of the AID/apobec/phorbolin family in humans (Jarmuz et al. (2002)). Indeed, overexpression of Apobec-1 is oncogenic in mice (Yamanaka S. et al. (1995)) and Apobec-1 family members are expressed in many tumour cell lines. The mutator activity demonstrate herein provides a molecular explanation for the mechanism for this oncogenesis. Tumour cells generally show an enhanced rate of mutation compared with non-tumour cells with mutations at dC/dG being the most common nucleoside substitutions. Thus, the ability to modulate gene products that trigger mutation provides a method of treating disorders characterised by an increased mutation rate, such as cancer.

Accordingly, in another aspect of the invention there is provided a method for treating a disorder characterised by increased mutations comprising treating an individual having such a disorder with an agent that modifies AID or AID homologue functional activity or gene expression. Suitably the disorder is selected from cancer, autoimmune disease or other disorders in which increased mutations are correlated with the disease phenotype.

In one embodiment said treatment may be prophylactic i.e. a preventative treatment. This is particularly applicable to treatment of an individual that may be predisposed to the development of a specific disorder. For example, an individual may be predisposed to develop a cancer through, for example, overexpression of AID or its homologues. In such an individual prophylactic treatment with an agent that modifies AID or AID homologue functional activity or gene expression may act to prevent the condition developing.

In a preferred embodiment of this aspect, the AID homologue is Apobec-1, Apobec-3G or Apobec-3C.

The development of resistance to antibiotics by a population of bacteria is a problem in treatment of everyday infections. The ability to decrease the rate at which mutations conferring the development of antibiotic resistance would be desirable. Understanding the role of AID in generating mutations along with the observation that bacterial cells express proteins having a similar activity to AID (see, for example, Shen et al. (1992); Navaratnam et al. (1998)) enables modification of an AID-like mutator activity in bacteria to modify the rate at which antibiotic resistance arises. Accordingly in another aspect of the invention there is provided a method of decreasing hypermutation/resistance to a compound such as an antibiotic in a population of bacteria by modulating bacterial AID-like activity.

DEFINITIONS

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). These documents are incorporated herein by reference.

The abbreviations used herein include: APOBEC1, apolipoprotein B editing complex catalytic subunit 1; AID, activation-induced deaminase; TLC, thin-layer chromatography; PEI, polyethylene imine; UDG, uracil-DNA glycosylase.

The terms "variant" or "derivative" in relation to AID polypeptide includes any substitution of, variation of, modification of, replacement of, deletion of or addition of one (or more) amino acids from or to the polypeptide sequence of AID. Preferably, nucleic acids-encoding AID are understood to comprise variants or derivatives thereof.

Such "modifications" of AID polypeptides include fusion proteins in which AID polypeptide or a portion or fragment thereof is linked to or fused to another polypeptide or molecule.

The term "homologue" as used herein with respect to the nucleotide sequence and the amino acid sequence of AID may be synonymous with allelic variations in the AID sequences and includes the known homologues, for example, Apobec-1 and other Apobec homologues including Apobec3C, Apobec3G, phorbolin and functional homologues thereof.

The "functional activity" of a protein in the context of the present invention describes the function the protein performs in its native environment. Altering or modulating the functional activity of a protein includes within its scope increasing, decreasing or otherwise altering the native activity of the protein itself. In addition, it also includes within its scope increasing or decreasing the level of expression and/or altering the intracellular distribution of the nucleic acid encoding the protein, and/or altering the intracellular distribution of the protein itself. By "AID mutation activity" or "mutator activity" is meant the functional activity of AID or its homologues to increase mutation above background.

The term "expression" refers to the transcription of a genes DNA template to produce the corresponding mRNA and translation of this mRNA to produce the corresponding gene product (i.e., a peptide, polypeptide, or protein). The term "activates gene expression" refers to inducing or increasing the transcription of a gene in response to a treatment where such induction or increase is compared to the amount of gene expression in the absence of said treatment. Similarly, the terms "decreases gene expression" or "down-regulates gene expression" refers to inhibiting or blocking the transcription of a gene in response to a treatment and where such decrease or down-regulation is compared to the amount of gene expression in the absence of said treatment.

The "mutation rate" is the rate at which a particular mutation occurs, usually given as the number of events per gene per generation whereas "mutation frequency" is the frequency at which a particular mutant is found in the population.

"Hypermutation" or "increased mutation rate" or "increased mutation frequency" refers to the mutation of a nucleic acid in a cell at a rate above background. Preferably, hypermutation refers to a rate of mutation of between $10^{-5}$ and $10^{-3}$ $bp^{-1}$ $generation^{-1}$. This is greatly in excess of background mutation rates, which are of the order of $10^{-9}$ to $10^{-10}$ mutations $bp^{-1}$ $generations^{-1}$ (Drake et al., 1998 Genetics 148:1667-1686) and of spontaneous mutations observed in PCR. 30 cycles of amplification with Pfu polymerase would produce <$0.05 \times 10^{-3}$ mutations $bp^{-1}$ in the product, which in the present case would account for less than 1 in 100 of the observed mutations (Lundberg et al., 1991 Gene 108:1-6.

In vivo, hypermutation is a part of the natural generation of immunoglobulin diversity through generating variable chain (V) genes. According to one aspect of the present invention therefore, the cell line is preferably an immunoglobulin-producing cell line which is capable of producing at least one immunoglobulin V gene. A V gene may be a variable light chain ($V_L$) or variable heavy chain ($V_H$) gene, and may be produced as part of an entire immunoglobulin molecule; it may be a V gene from an antibody, a T-cell receptor or another member of the immunoglobulin superfamily. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). Thus, preferred cell lines according to the invention are derived from B-cells. According to the present invention, it has been determined that cell lines derived from antibody-producing B cells may be isolated which retain the ability to hypermutate V region genes, yet do not hypermutate other genes.

"Class switching" or "switch recombination" is the recombination process in V gene rearrangement that leads to a change in the constant region of the expressed antibody. "Gene conversion" is an additional mechanism in the recombination process which is found to occur in chicken and rabbits (but not in human or mouse) and contributes to V gene diversification.

The term "constitutive hypermutation" refers to the ability of certain cell lines to cause alteration of the nucleic acid sequence of one or more specific sections of endogenous or transgene DNA in a constitutive manner, that is without the requirement for external stimulation. Generally, such hypermutation is directed. In cells capable of directed constitutive hypermutation, sequences outside of the specific sections of endogenous or transgene DNA are not subjected to mutation rates above background mutation rates. The sequences which undergo constitutive hypermutation are under the influence of hypermutation-recruiting elements, as described further below, which direct the hypermutation to the locus in question. Thus in the context of the present invention, target nucleic acid sequences, into which it is desirable to introduce mutations, may be constructed, for example by replacing V gene transcription units in loci which contain hypermutation-recruiting elements with another desired transcription unit, or by constructing artificial genes comprising hypermutation-recruiting elements.

The cell population which is subjected to selection by the method of the invention may be a polyclonal population, comprising a variety of cell types and/or a variety of target sequences, or a (mono-) clonal population of cells.

A clonal cell population is a population of cells derived from a single clone, such that the cells would be identical save for mutations occurring therein. Use of a clonal cell population preferably excludes co-culturing with other cell types, such as activated T-cells, with the aim of inducing V gene hypermutation.

BRIEF DESCRIPTION OF THE TABLES AND FIGURES

Table 1 shows the results of experiments in which AID was expressed in *E. coli*.

Table 2 shows the results of experiments in which AID and its homologues, Apobec-1, Apobec3C and Apobec3G were expressed in *E. coli*.

Table 3 shows the results of a second set of experiments in which AID and its homologues, Apobec-1, Apobec 2, Apobec3C and Apobec3G were expressed in *E. coli*.

Table 4 shows the oligonucleotides used in Example 3.

FIGURE LEGENDS

FIG. 1 DNA deamination model of Ig gene diversification. For details, see text.

FIG. 2 Expression of AID in *E. coli* yields a mutator phenotype that is enhanced by UDG-deficiency. (a) Frequencies of $Rif^R$ mutants generated following overnight culture (±IPTG) of *E. coli* KL16 carrying either the AID expression plasmid or the vector control. Each point represents the mutation frequency of an independent overnight culture. The fold enhancement by AID expression is indicated. (b) Mutation frequency of AID- and vector-transformed, UDG-deficient KL16 ung-1 cells. Performed and labeled as in (a), but note the differing y-axis scale. (c) Photograph of representative plates. The mutation frequency relative to the vector-transformed wildtype control is indicated in the centre of each plate. See Table 1 for additional data.

FIG. 3 Nature of the AID-induced RifR mutants. (a) Comparison of the distribution of independent rpoB mutations identified in RifR colonies obtained from AID- and vector-transformed cells. The data are combined from results obtained using both KL16 and AB1157 hosts, but the two hosts show no difference in their mutation 10 spectrum. The underlined sequence (nucleotide sequence shown in SEQ. ID. NO.: 23; amino acid sequence shown in SEQ. ID. NO.: 24) is the region of rpoB which is known (din & Zhou (1996)) to harbour the majority of mutations conferring RifR. Less than 5% of the RifR sequenced clones did not show any mutations in this region. (b) Comparison of the types of rpoB nucleotide substitutions identified.

FIG. 4 Comparison of the independent gyrA mutations identified in NalR colonies of AID- and vector-transformed *E. coli* KL16. Less than 5% of the NalR clones analysed failed to show mutations in the sequenced region (nucleotide sequence shown in SEQ. ID. NO.: 25; amino acid sequence shown in SEQ. ID. NO.: 26).

FIG. 5

(a) Frequencies of $Rif^R$ mutants generated following overnight culture of cells carrying an APOBEC1 or AID expression construct or the vector control. Each point represents the mutation frequency of an independent overnight culture. The median mutation frequency and the fold enhancement by expression of the mutator are indicated in which AID and its homologues, Apobec-1, Apobec3C and Apobec3G were expressed in *E. coli*

(b) Effect of IPTG on APOBEC1-induced mutation to $Rif^R$. The mutation observed in the absence of IPTG may well be due to pTrc99A promoter leakiness. Labeled as in (a).

(c) Single amino acid changes in APOBEC1 abrogate its ability to stimulate mutation to $Rif^R$. Labeled as in (a).

(d) Comparison of average growth rates of vector- and APOBEC1 transformed cells propagated in the presence of the inducer IPTG. Five independent cultures were used for each measurement, but the standard deviations proved smaller than the symbols.

FIG. 6 Spectrum of RifR mutations found in cells expressing APOBEC 1.

(a) Comparison of the distribution of independent $Rif^R$ mutations within the region of rpoB sequenced (SEQ. ID. NO.: 27) found in cells transformed with vector alone or an APOBEC1 expression construct. The preferred sites in AID-expressing cells are highlighted by dark boxes.

(b) Summary of the types of nucleotide substitutions in rpoB identified in RifR vector- and APOBEC1-transformed cells given as a percentage of the total database (120 from controls and 136 from APOBEC1-transformed cells).

FIG. 7 APOBEC1, APOBEC3C and APOBEC3G all stimulate mutation at dC/dG but with distinct target specificities.

(a) Schematic of the APOBEC1 family of mutator proteins depicting the putative zinc-binding deaminase motif and the conserved leucine-rich region. Other APOBEC1 family members also contain either single (APOBEC2 and APOBEC3A) or double (APOBEC3B and APOBEC3F) putative zinc-binding motifs (Madsen et al.). APOBEC3D and APOBEC3E may be a single protein with two zinc-binding regions as evidenced by IMAGE clone 3915193 or two separate, single zinc-binding motif proteins (Jarmuz et al.). For each protein, the enhancement of mutation to $Rif^R$ yielded by that protein (data from Table 3), the percentage of the mutations observed that were nucleotide transitions at dC or dG and the identity of the major rpoB mutational hotspots observed (the percentage of the total number of rpoB mutations observed at that hotspot given in parentheses) are all given. The total number of mutated rpoB sequences analysed (n) for each APOBEC1 family member is given.

(b) Distribution of rpoB mutations in Rif$^R$ mutants obtained using bacteria transformed with different APOBEC family members. There are 26 sites within the sequenced region of rpoB where a single nucleotide substitution can yield Rif$^R$; at 11 of these sites, Rif$^R$ can be achieved by a transition at dC or dG. The percentage of the total number of Rif$^R$ mutations obtained with each APOBEC family member that occurred at each of these 11 sites is indicated. Mutations at other sites are not indicated (an omission which is mainly of significance to the depiction of the vector control).

FIG. 8a shows pRB700 construct comprising the *Bacillus subtilis* gene SacB under the control of the *E. coli* promoter for PhoB.

FIG. 8b shows the pRB740 construct comprising a variant SacB cassette under the control of the PhoB promoter and also under the control of the strong IPTG inducible Trc promoter downstream and in the opposite orientation.

FIG. 9 shows the results of mutation analysis in mutants in the SacB cassette.

FIG. 10b shows the results of mutation frequency analysis. pRB700 and pRB740 are described in FIG. 9. Vector control and APOBEC-1 expression plasmids pTrc99a and pRH200 are as described (Harris et al 2002 Mol Cell. 10(5):1247-53). Growth media all include 100 μg/ml carbenicillin and 1 mM IPTG to maintain and induce expression plasmids. LB=Luria Bertani medium. Min MOPS=Minimal MOPS medium (Neidhardt et al 1974. Culture medium for enterobacteria. J Bacteriol. 119:736-47) using 0.1% glycerol as carbon source supplemented with 2 μM Zn$^{2+}$ and 0.1% casamino-acids (C, D, G, H) or bacto-peptone (I).

FIG. 11 shows a table of results for mutation analysis.

Figure 12:
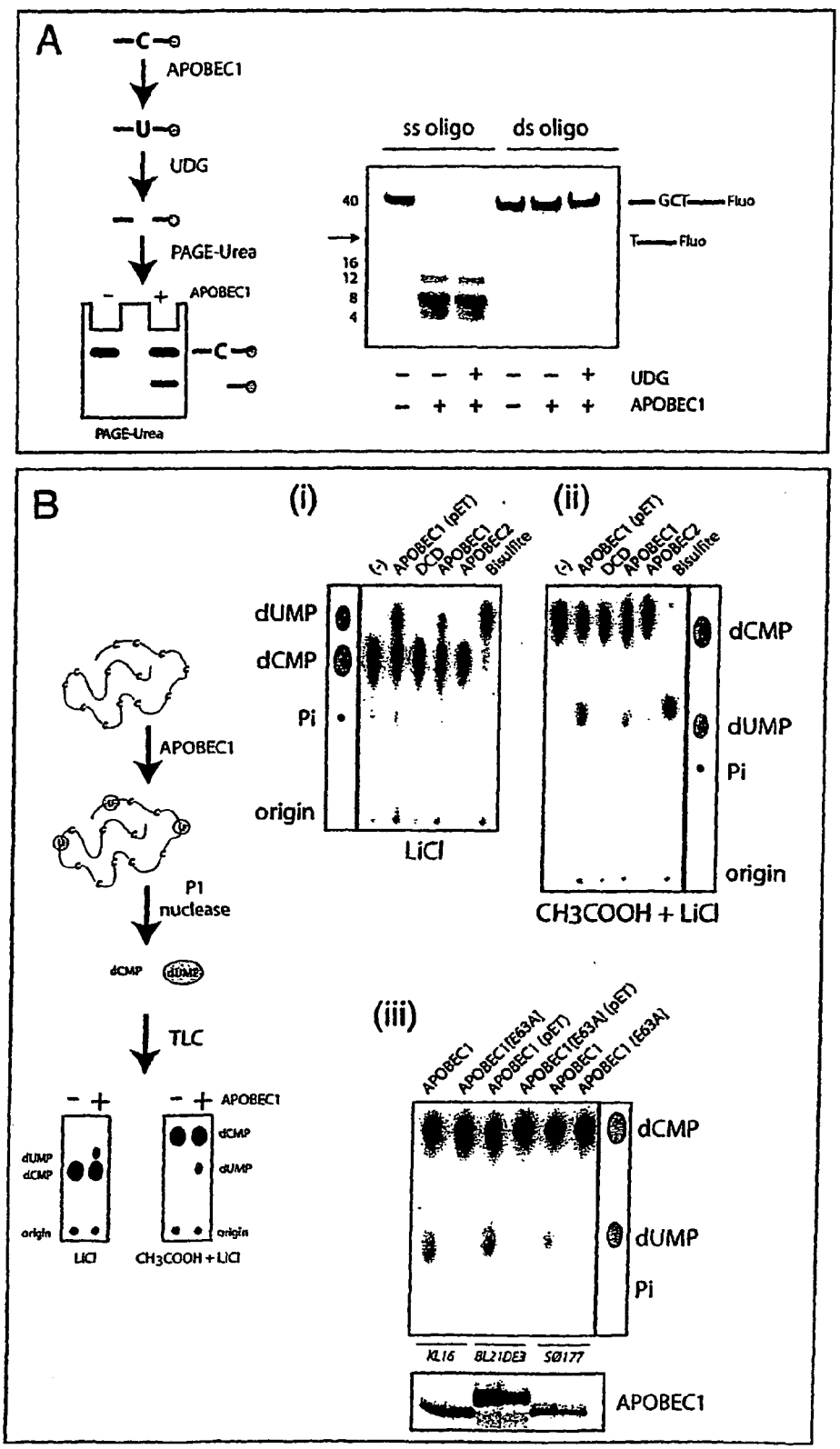

FIG. 12 shows the results of assaying for DNA deaminase activity in crude extracts using the TLC-based assay.

A, Schematic representation of the TLC-based deaminase assay. α-[$^{32}$P]dCMP-labelled single-stranded DNA was incubated with the indicated extracts, purified, digested with P1 nuclease and analysed by TLC in one of two buffer systems.

B, Analysis by TLC in either the LiCl [panel (i)] or CH$_3$COOH+LiCl [panels (ii) and (iii)] buffer systems of the assay products of α-[$^{32}$P]dCMP-labelled single-stranded DNA incubated with sonic extracts of *E. coli* transformants that carry plasmids directing the overexpression of APOBEC1, APOBEC2, a mutant APOBEC1 (harbouring an E63→A substitution) or dCTP deaminase (DCD). Controls are provided by extracts from *E. coli* transformed with vector only (−) as well as by substrate DNA that has been subjected to chemical deamination using bisulfite. The plasmid/host strain combination used for recombinant protein expression was pTrc99/*E. coli* KL16 except where (as indicated) the pET vector was used (in which case the host strain was BL21DE3) or where activity was monitored using the *E. coli* SØ177 host (which is deficient in both dcd and cdd deaminases). The migration of dUMP, dCMP and [$^{32}$P] inorganic phosphate (Pi) markers is indicated. The abundance of wild-type and E63→A mutant APOBEC1 polypeptides in extracts was monitored by Western [lower part of panel (iii)].

Figure 13:
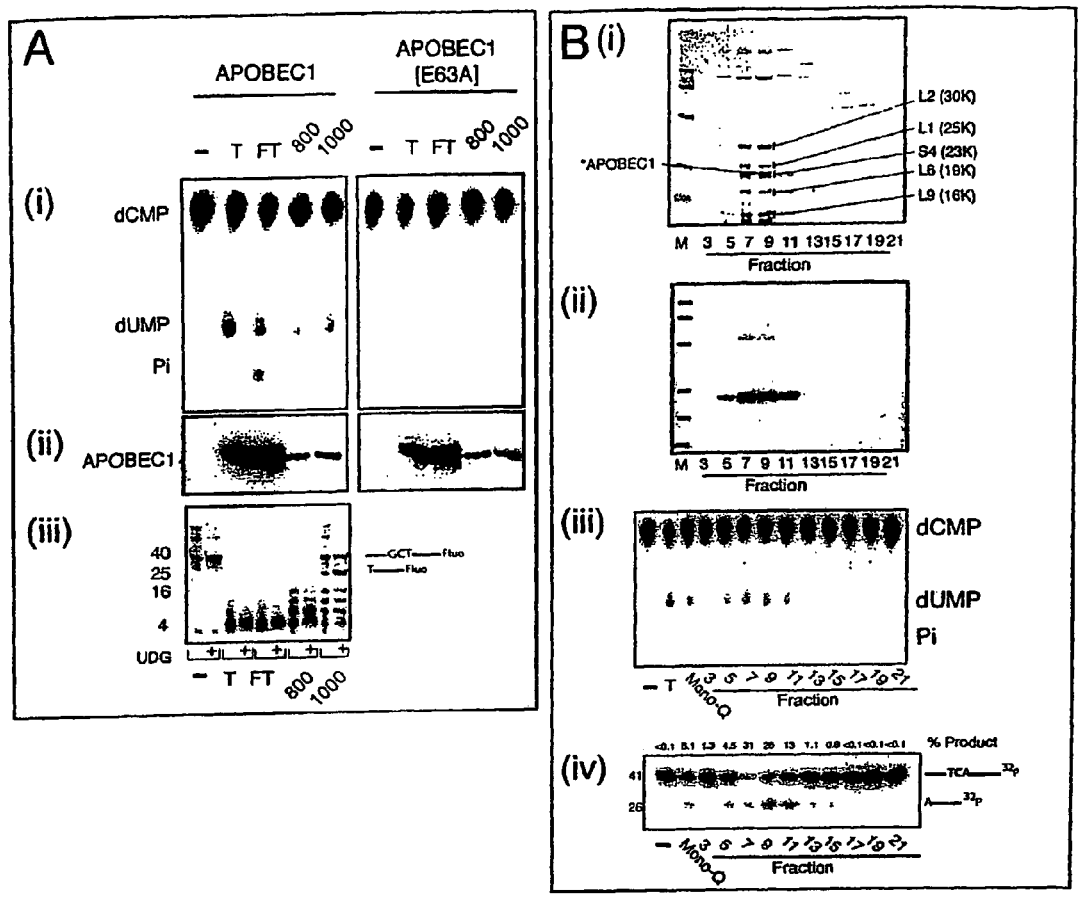

FIG. 13 shows APOBEC1 fractionation.

A, Ion-exchange chromatography on Sepharose Mono-Q. Clarified lysates of APOBEC1 (and APOBEC1 [E63→A])-expressing *E. coli* were loaded onto Mono-Q. The presence of APOBEC1 polypeptide was detected by Western blot [panel (ii)]. Deaminase activity was monitored by both TLC- and UDG-based assays [panels (i) and (iii)] in the total lysate (T), the flow through (FT) and in the 800 and 1000 mM-salt washes.

B, Gel filtration of the concentrated high (>1 M) salt eluate from the Mono-Q column on Sephacryl S200. Fractions were analysed by: (i) SDS/PAGE; bands were excised and analysed by MALDI-TOF following in gel trypsin digestion. The bands yielding peptide sequences derived from APOBEC1 and ribosomal proteins L1, 2, 6 and 9 and S4 are indicated. M, molecular weight markers. (ii) Western blotting for APOBEC1; (iii) TLC-based and (iv) UDG-based deaminase assays, which were performed on samples of the total clarified bacterial lysate (T) as well as on the eluate from the Mono-Q. The UDG-based deaminase assay was performed using 3'-α-[$^{32}$P]-labelled SPM274; note that some of the 3'-label is removed during the incubation. The percentage of label associated with the 26-base product of the deamination/cleavage (as opposed to 40-base input oligonucleotide) is indicated.

Figure 14:
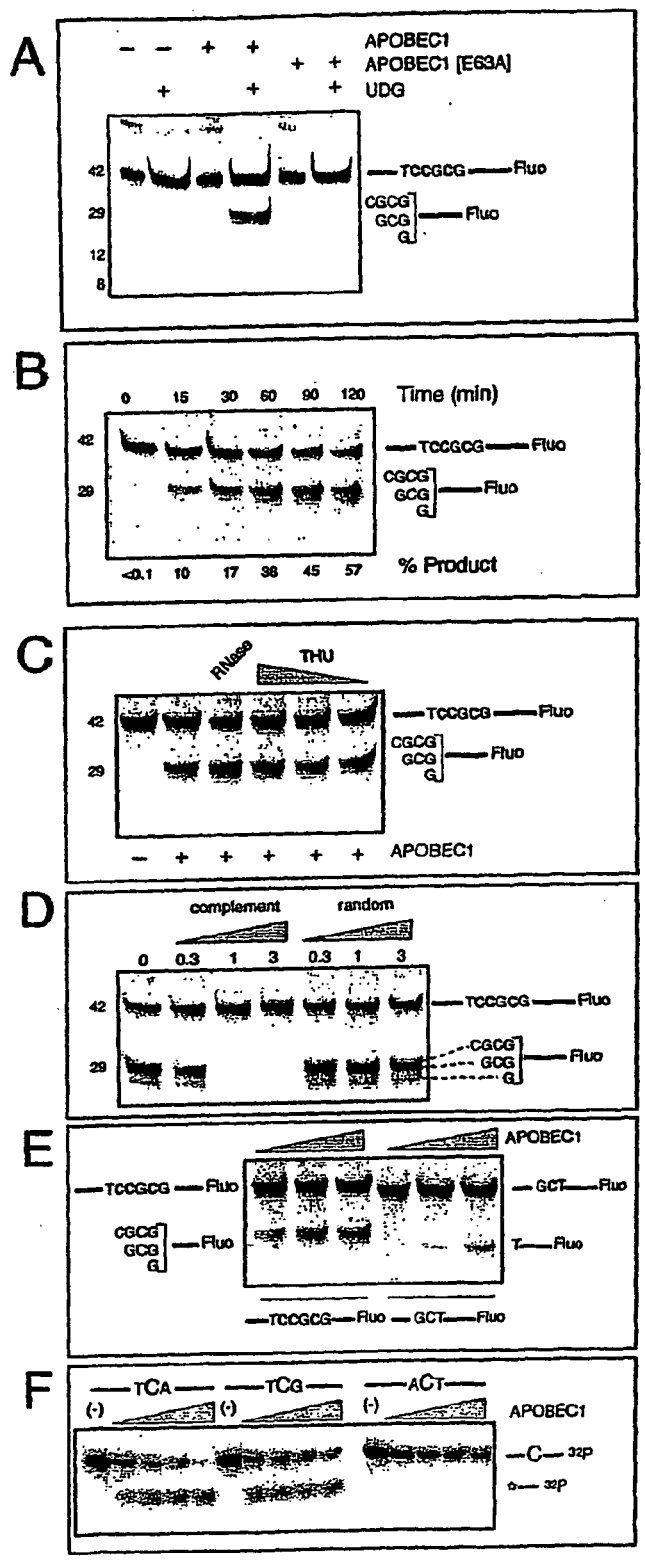

FIG. 14 shows specificity of APOBEC1-mediated DNA deamination using the UDG-based assay.

A, Schematic representation of the UDG-based deaminase assay. 5'-biotinylated (circle) oligonucleotides that were 3'labelled (asterisk) with fluorescein or α-[$^{32}$P]dideoxyadenylate were incubated with APOBEC1-containing (or control) samples prior to streptavidin purification, UDG-treatment and PAGE-urea analysis.

B, Partially purified APOBEC1 as well as the E63→A mutant were tested for their ability to deaminate 3'-fluorescein conjugated oligonucleotide SPM168 using the UDG-based assay. The fluorescence scan of the gel, including controls performed without UDG treatment or without APOBEC1, is shown with the positions of the expected products and size markers indicated.

C, Time-course of SPM168 deamination by partially purified APOBEC1.

D, Inclusion of RNAase (1 μg) or of tetrahydrouridine (THU; 20 nmoles, 2 nmoles, or 200 pmoles) does not inhibit the activity of APOBEC1.

E, Deaminating activity is specific for a single-stranded substrate. The assay was performed using 3'-fluorscein-labelled oligonucleotide SPM168 in the presence of the indicated ratio of either oligonucleotide SPM171 (which is complementary to SPM168) or SPM201 (which is not).

F, Comparison of 3'-fluorescein labelled oligonucleotides SPM168 (left three lanes) and SPM163 (right three lanes) as targets for deamination by 0.5, 1 and 2 μl of APOBEC1.

Figure 15:
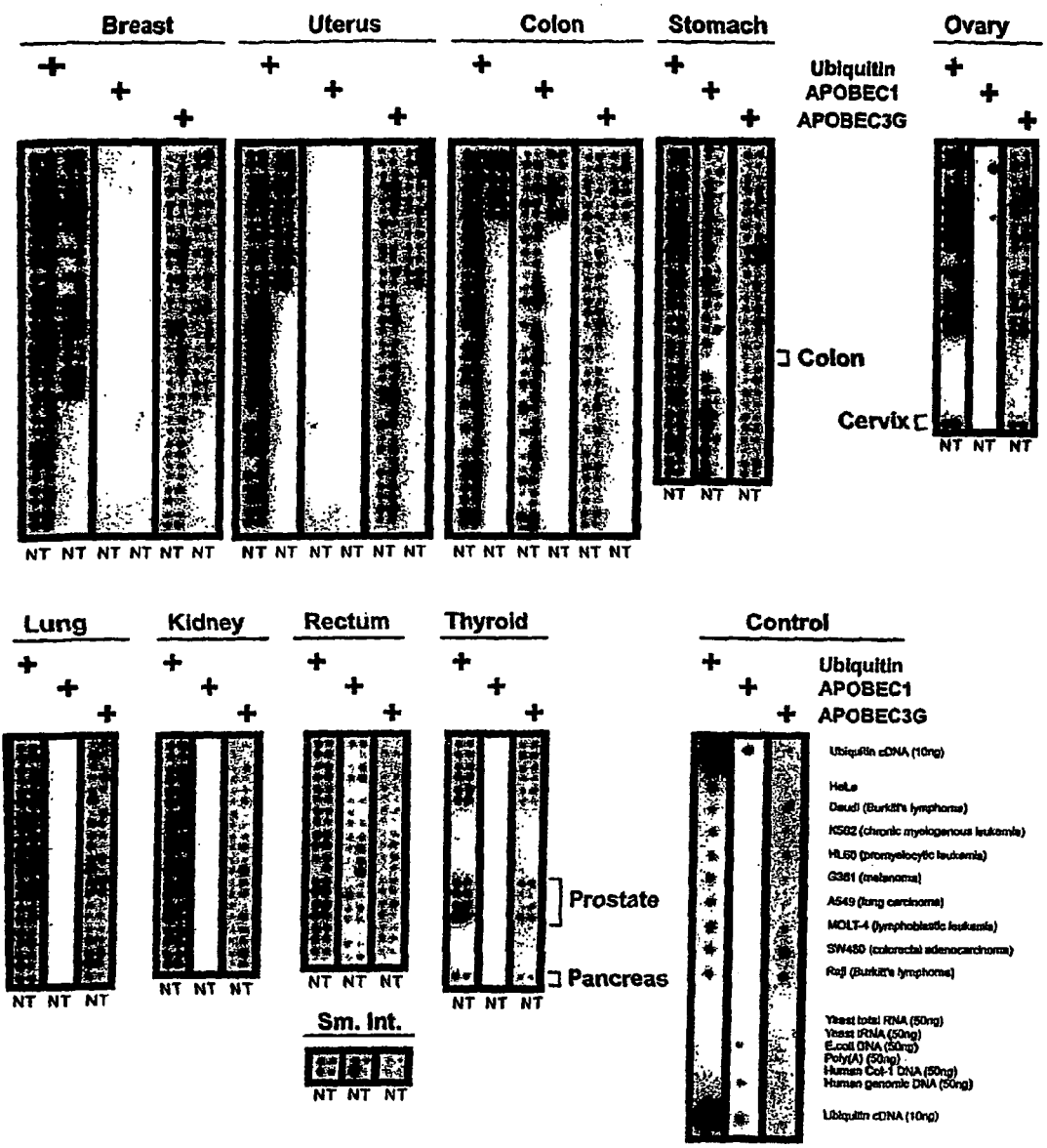

FIG. 15 Autoradiographs showing hybridisation of APOBEC1, APOBEC3G, and ubiquitin (control) probes to matched pairs of tumour (T) and corresponding normal (N) cDNA samples derived from a variety tissues using a cancer profiling array (Clontech).

DETAILED DESCRIPTION OF THE INVENTION

Figure 1:
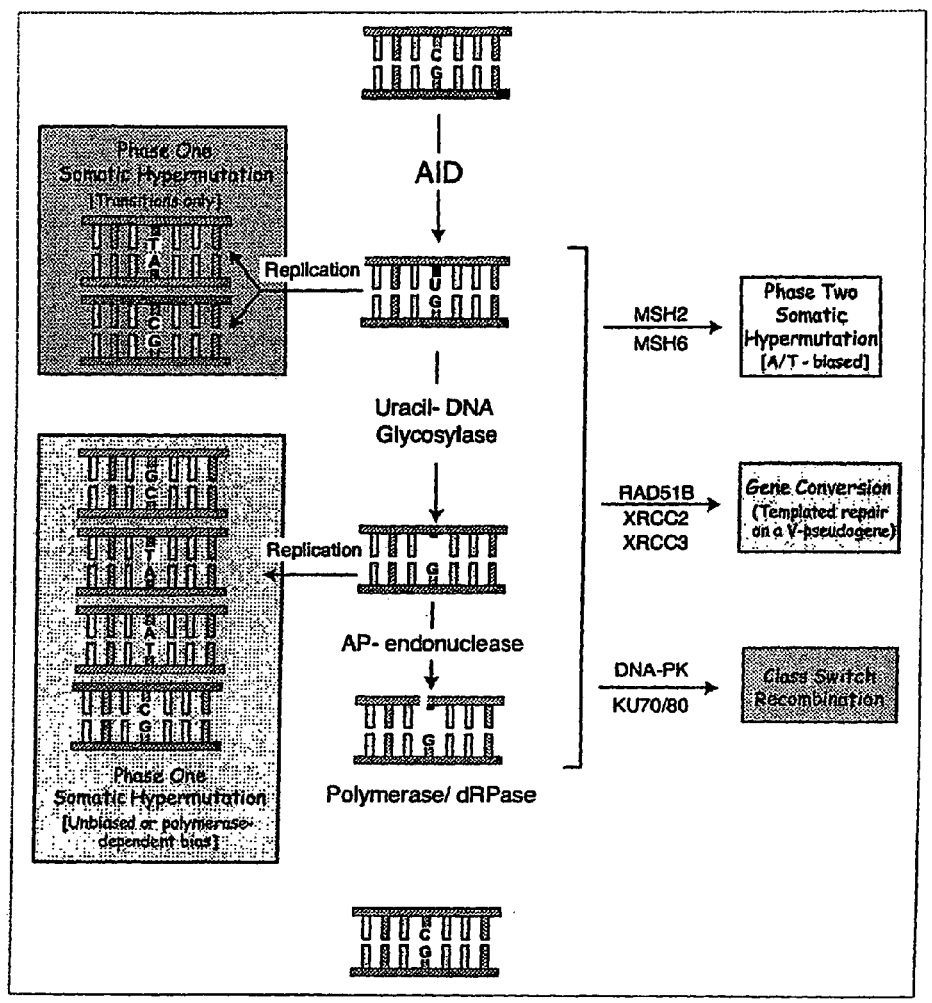

The fact that AID, a homologue of Apobec-1 (which deaminates C in RNA), is required for all three programmes of diversification of rearranged immunoglobulin genes (Muramatsu M. et al. (2000); Revy, P. et al. (2000); Arakawa, H. et al. (2002); Harris, R. S. et al. (2002) and Martin, A. et al. (2002)) and that the initiation of all three programmes could be explained by DNA modification at dG/dC (Martin et al. (2002), Maizels et al. (1995), Weill et al. (1996); Sale et al. (2001), Ehrenstein et al. (1999) Rada et al. (1998) and Wiesendanger et al. (2000)) led the present inventors to the model presented in FIG. 1. The hypothesis set out herein is that AID mediates the deamination of a small number of C residues within the Ig loci. Conventionally, this would trigger base excision repair (Lindahl T. (2000)) with uracil being removed by uracil-DNA glycosylase (UDG) and, following cleavage at the abasic site by an apyrimidic endonuclease (APE), a dC residue would be reinserted by a DNA polymerase/deoxyribophosphodiesterase. If, instead of being repaired, the DNA strand harbouring the dU residue were used to template DNA synthesis, then the consequence would be a dC→dT (and dG→dA) transition. Alternatively, if DNA synthesis occurred over the abasic site, both transitions and transversions would be generated although a transition bias might still be observed if the polymerase used for the lesion bypass preferentially inserted dA residues. Thus, the stage at which polymerase bypass of the original lesion occurred as well as the preferences of the polymerase used would affect the transition bias of the hypermutation. This could account for the otherwise puzzling observation that whereas mutation in mouse and man as well as in the hypermutating Ramos B cell line exhibits a marked transition preference (Sale et al. (1998)), no such preference is evident in the mutations exhibited by the XRCC2-deficient chicken DT40 B cell line (Sale et al. (2001)).

Templated repair of the deamination-induced lesion by a V pseudogene would lead to gene conversion; such repair would be dependent on the RAD51 paralogues XRCC2, XRCC3 and RAD51B (Sale et al. (2001)). The second phase of mutation (yielding mutations at dA/dT) which is observed in vivo in man and mouse would be triggered by MSH2/MSH6 recognition of the dU/dG mismatch itself or of some intermediate in its correction (Rada et al. (1998); Wiesendanger et al. (2000)), and would presumably occur by some form of patch repair. Repair partnered on another switch region could lead to switch recombination. For switching, where there is an indication for a role of non-homologous end-joining (Manis et al. (2002); Peterson et al. (2001)), one might imagine that deamination of proximal dCs on opposite strands could generate the staggered DNA breaks proposed by Chen et al (2001).

A central prediction of this model is that AID has the ability to trigger dC→dU deamination in DNA. Such an activity would presumably be largely restricted to its physiological target (the Ig loci) since a rampant DNA deaminase activity would likely be harmful to the cell.

The results presented herein suggest that, whereas functional Ig genes are generated by RAG-mediated rearrangement, subsequent diversification is triggered by AID-mediated deamination of dC residues within the immunoglobulin locus with the outcome (gene conversion, switch recombination or mutation phases ½) dependent upon the way in which the initiating dU/dG lesion is resolved.

As well as AID, the APOBEC/AID family contains several members that are capable of mutating DNA, triggering nucleotide substitutions at dC/dG by a process which, given its sensitivity to uracil-DNA glycosylase, is likely to be dC deamination.

The physiological functions of the other APOBEC family members are unknown. Whereas APOBEC1 shows relatively restricted tissue distribution, APOBEC3G is much more widely expressed. Hybridisation experiments suggest that some APOBEC family members are well expressed in a variety of cancers (FIG. 8) and cancer cell lines.

Quite apart, however, from the normal physiological functions of the APOBEC family members, the fact that several of the members can display a DNA mutator activity (taken together with the observation that transgenic expression of APOBEC1 is oncogenic in mice) raises the possibility that they might contribute to the 'spontaneous' dC deamination that occurs in normal cells as well as the elevated mutation rates proposed to be associated with many human cancers. Indeed, in the large database of p53 mutations in human cancers (where nearly 13,000 single base changes have been identified scattered over a large number of positions in the gene) over 50% of the substitution mutations (and over 60% of the silent mutations) are nucleotide transitions at dC/dG with roughly half of these dC/dGs being at dC/dG dinucleotides.

Measuring an Enhanced Mutation Rate in Cells as an Indication of a Mutator Phenotype Hypermutating cells or cells having a mutator phenotype may be identified by a variety of techniques, including sequencing of target sequences, selection for expression loss mutants, assay using bacterial MutS protein and selection for change in gene product activity. Methods for measuring mutation rates include fluctuation analysis (described, for example, by Luria and Delbreck (1943) and Capizzi and Jameson (1973)). In this, the generation of clones showing resistance to a selection media. Suitable selection media for prokaryotic cells include rifampicin, nalidixic acid, valine and fucose. Cells selected according to this procedure are cells in which mutation has occurred in a gene or genes which enable the effect of the selection media to be overcome. Other ways of determining mutation rates include direct sequencing of specific portions of DNA or indirect methods such as the MutS assay (Jolly et al., 1997 Nucleic Acids Research 25, 1913-1919) or monitoring the generation of immunoglobulin loss variants.

In a preferred embodiment of the invention, the method involves generating mutations in a target nucleic acid which encodes an immunoglobulin. Immunoglobulin loss may be detected both for cells which secrete immunoglobulins into the culture medium, and for cells in which the immunoglobulin is displayed on the cell surface. Where the immunoglobulin is present on the cell surface, its absence may be identified for individual cells, for example by FACS analysis, immunofluorescence microscopy or ligand immobilisation to a support. In a preferred embodiment, cells may be mixed with antigen-coated magnetic beads which, when sedimented, will remove from the cell suspension all cells having an immunoglobulin of the desired specificity displayed on the surface.

The technique may be extended to any immunoglobulin molecule, including antibodies, T-cell receptors and the like. The selection of immunoglobulin molecules will depend on the nature of the clonal population of cells which it is desired to assay according to the invention.

Alternatively, mutations in cells according to the invention may be identified by sequencing of target nucleic acids, such as V genes, and detection of mutations by sequence comparison. This process may be automated in order to increase throughput.

In a further embodiment, cells which hypermutate V genes may be detected by assessing change in antigen binding activity in the immunoglobulins produced in a clonal cell population. For example, the quantity of antigen bound by a specific unit amount of cell medium or extract may be assessed in order to determine the proportion of immunoglobulin produced by the cell which retains a specified binding activity. As the V genes are mutated, so binding activity will be varied and the proportion of produced immunoglobulin which binds a specified antigen will be reduced.

Alternatively, cells may be assessed in a similar manner for the ability to develop a novel binding affinity, such as by exposing them to an antigen or mixture of antigens which are initially not bound and observing whether a binding affinity develops as the result of hypermutation.

In a further embodiment, the bacterial MutS assay may be used to detect sequence variation in target nucleic acids. The MutS protein binds to mismatches in nucleic acid hybrids. By creating heteroduplexes between parental nucleic acids and those of potentially mutated progeny, the extent of mismatch formation, and thus the extent of nucleic acid mutation, can be assessed.

Where the target nucleic acid encodes an gene product other than an immunoglobulin, selection may be performed by screening for loss or alteration of a function other than binding. For example, the loss or alteration of an enzymatic activity may be screened for.

Genetic Manipulation of Cells

Cells modified to express AID or its homologues are cells in which AID protein expression (or AID homologue protein expression) has been induced by means, for example, of transfecting host cells with a vector encoding AID protein. Such transfection may be stable or transient transfection.

"Vector" refers to any agent such as a plasmid, cosmid, virus, autonomously replicating sequence, phage, or linear single-stranded, circular single-stranded, linear double stranded, or circular double-stranded DNA or RNA nucleotide sequence that carries exogenous DNA into a host cell or organism. The recombinant vector may be derived from any source. In the context of the present invention, the vector is for stable expression of AID and is, therefore, capable of genomic integration or autonomous replication but maintained throughout division cycles of the host cell.

An expression vector includes any vector capable of expressing a coding sequence encoding a desired gene product that is operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding a heterologous coding sequence may be inserted into a vector suitable for expression of cDNAs in mammalian cells, e.g. a CMV enhancer-based vector such as pEVRF (Matthias, et al., 1989).

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene product expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

Vector-driven protein expression can be constitutive or inducible. Inducible vectors include either naturally inducible promoters, such as the trc promoter, which is regulated by the lac operon, the IPTG promoter which is inducible by IPTG and the pL promoter, which is regulated by tryptophan, the MMTV-LTR promoter, which is inducible by dexamethasone, or can contain synthetic promoters and/or additional elements that confer inducible control on adjacent promoters. Other promoters include E. coli promoters such as PhoB.

Methods for introducing the vectors and nucleic acids into host cells are well known in the art the choice of technique will depend primarily upon the specific vector to be introduced and the host cell chosen. Plasmid vectors will typically be introduced into chemically competent or electrocompetent bacterial cells. Vectors can be introduced into yeast cells by spheroplasting, treatment with lithium salts, electroporation, or protoplast fusion. Mammalian and insect cells can be directly infected by packaged viral vectors, or transfected by chemical or electrical means.

Methods for Generating Fusion Proteins

AID or any of its homologues or derivatives, including Apobec-1, may be generated as fusion proteins comprising the AID protein or a portion that retains its mutator activity coupled to a DNA binding domain or one half of a specific binding pair. Preferably the fusion protein will not hinder the mutator activity of the protein sequence. Methods for generating fusion proteins will be familiar to those skilled in the art and include generation of expression vectors comprising the AID nucleic acid sequence linked or ligated to the nucleic acid sequence encoding a DNA binding domain.

Methods for Preparing and Selecting Immunoglobulins or Other Surface Expressed Proteins.

The process of hypermutation is employed, in nature, to generate improved or novel binding specificities in immunoglobulin molecules. Thus, by selecting cells according to the invention which produce immunoglobulins capable of binding to the desired antigen and then propagating these cells in order to allow the generation of further mutants, cells which express immunoglobulins having improved binding to the desired antigen may be isolated.

A variety of selection procedures may be applied for the isolation of mutants having a desired specificity. These include Fluorescence Activated Cell Sorting (FACS), cell separation using magnetic particles, antigen chromatography methods and other cell separation techniques such as use of polystyrene beads.

Separating cells using magnetic capture may be accomplished by conjugating the antigen of interest to magnetic particles or beads. For example, the antigen may be conjugated to superparamagetic iron-dextran particles or beads as supplied by Miltenyi Biotec GmbH. These conjugated particles or beads are then mixed with a cell population which may express a diversity of surface immunoglobulins. If a particular cell expresses an immunoglobulin capable of binding the antigen, it will become complexed with the magnetic beads by virtue of this interaction. A magnetic field is then applied to the suspension which immobilises the magnetic particles, and retains any cells which are associated with them via the covalently linked antigen. Unbound cells which do not become linked to the beads are then washed away, leaving a population of cells which is isolated purely on its ability to bind the antigen of interest. Reagents and kits are available from various sources for performing such one-step isolations, and include Dynal Beads (Dynal A S; http://www.dynal.no), MACS-Magnetic Cell Sorting (Miltenyi Biotec GmbH; http://www.miltenyibiotec.com), CliniMACS (AmCell; http://www.amcell.com) as well as Biomag, Amerlex-M beads and others. Similar techniques can be used for non-immunoglobulin surface expressed molecules where selection for their surface expression can be through recognition by a specific binding partner.

Fluorescence Activated Cell Sorting (FACS) can be used to isolate cells on the basis of their differing surface molecules, for example surface displayed immunoglobulins. Cells in the sample or population to be sorted are stained with specific fluorescent reagents which bind to the cell surface molecules. These reagents would be the antigen(s) of interest linked (either directly or indirectly) to fluorescent markers such as fluorescein, Texas Red, malachite green, green fluorescent protein (GFP), or any other fluorophore known to those skilled in the art. The cell population is then introduced into the vibrating flow chamber of the FACS machine. The cell stream passing out of the chamber is encased in a sheath of buffer fluid such as PBS (Phosphate Buffered Saline). The stream is illuminated by laser light and each cell is measured for fluorescence, indicating binding of the fluorescent labelled antigen. The vibration in the cell stream causes it to break up into droplets, which carry a small electrical charge. These droplets can be steered by electric deflection plates under computer control to collect different cell populations according to their affinity for the fluorescent labelled antigen. In this manner, cell populations which exhibit different affinities for the antigen(s) of interest can be easily separated from those cells which do not bind the antigen. FACS machines and reagents for use in FACS are widely available from sources world-wide such as Becton-Dickson, or from service providers such as Arizona Research Laboratories (http://www.arl.arizona.edu/facs/).

Another method which can be used to separate populations of cells according to the affinity of their cell surface protein(s) for a particular antigen is affinity chromatography. In this method, a suitable resin (for example CL-600 Sepharose, Pharmacia Inc.) is covalently linked to the appropriate antigen. This resin is packed into a column, and the mixed population of cells is passed over the column. After a suitable period of incubation (for example 20 minutes), unbound cells are washed away using (for example) PBS buffer. This leaves only that subset of cells expressing immunoglobulins which bound the antigen(s) of interest, and these cells are then eluted from the column using (for example) an excess of the antigen of interest, or by enzymatically or chemically cleaving the antigen from the resin. This may be done using a specific protease such as factor X, thrombin, or other specific protease known to those skilled in the art to cleave the antigen from the column via an appropriate cleavage site which has previously been incorporated into the antigen-resin complex. Alternatively, a non-specific protease, for example trypsin, may be employed to remove the antigen from the resin, thereby releasing that population of cells which exhibited affinity for the antigen of interest.

Insertion of Heterologous Transcription Units

In order to maximise the chances of quickly selecting an antibody variant capable of binding to any given antigen, or to exploit the AID-dependant hypermutation system for non-immunoglobulin genes, a number of techniques may be employed to engineer cells according to the invention such that their hypermutating abilities may be exploited.

In a first embodiment, transgenes are transfected into a cell according to the invention such that the transgenes become targets for the directed hypermutation events.

As used herein, a "transgene" is a nucleic acid molecule which is inserted into a cell, such as by transfection or transduction. For example, a "transgene" may comprise a heterologous transcription unit as referred to above, which may be inserted into the genome of a cell at a desired location. The "transgene" may be the nucleic acid encoding the gene product of interest.

The plasmids used for delivering the transgene to the cells are of conventional construction and comprise a coding sequence, encoding the desired gene product, under the control of a promoter. Gene transcription from vectors in cells according to the invention may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with the heterologous coding sequence, provided such promoters are compatible with the host system of the invention.

Transcription of a heterologous coding sequence by cells according to the invention may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to the coding sequence, but is preferably located at a site 5' from the promoter.

Advantageously, a eukaryotic expression vector may comprise a locus control region (LCR). LCRs are capable of directing high-level integration site independent expression of transgenes integrated into host cell chromatin, which is of importance especially where the heterologous coding sequence is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA.

Transgenes according to the invention may also comprise sequences which direct hypermutation. Such sequences have been characterised, and include those sequences set forth in Klix et al., (1998; Eur. J. Immunol. 28:317-326), and Sharpe et al., (1991; EMBO J. 10:2139-2145), incorporated herein by reference. Thus, an entire locus capable of expressing a gene product and directing hypermutation to the transcription unit encoding the gene product is transferred into the cells. The transcription unit and the sequences which direct hypermutation are thus exogenous to the cell. However, although exogenous the sequences which direct hypermutation themselves may be similar or identical to the sequences which direct hypermutation naturally found in the cell The endogenous V gene(s) or segments thereof may be replaced with heterologous V gene(s) by homologous recombination, or by gene targeting using, for example, a Lox/Cre system or an analogous technology or by insertion into hypermutating cell lines which have spontaneously deleted endogenous V genes. Alternatively, V region gene(s) may be replaced by exploiting the observation that hypermutation is accompanied by double stranded breaks in the vicinity of rearranged V genes.

Furthermore, enhanced targeting of mutation can be achieved by inducing convergent promoters upstream and downstream of the desired gene and therefore inducing transcription in both directions. Deamination of dC in vitro by APOBEC-1 has be demonstrated to be dependent on the single-strandedness of the substrate oligonucleotide as described herein. The increase in availability of single-stranded DNA can be induced by convergent transcription or by a combination of transcription and DNA bending caused by promoter activation. Suitable types of promoter include the PhoB promoter. Other Prokaryotic promoters include Activators (e.g. AraBAD, PhoA), Repressors. (e.g. Tet, Lac, Tip, Hybrid Lac/Trp such as Tac, pL, Regulatable hybrids of pL such as pL-tet) and Viral Polymerase (e.g. T7). Suitable Eukaryotic promoters include promoters recognised by RNA Polymerase I (e.g. 45S rDNA) RNA Polymerase II (e.g. Gal4, β-Actin or Viral, such as CMV-IE and Artificial, especially Tet-on, Tet-off) RNA Polymerase III)(e.g. H1 RNA, U6 snRNA).

DNA Binding Domain and Specific DNA Recognition Sequences

Transcription factors bind DNA by recognising specific target sequences generally located in enhancers, promoters, or other regulatory elements that affect a particular target gene. The target sequences for a number of transcription factors are well known to those skilled in the art. Transcription factors having specific DNA target or recognition sequences include the yeast transcription factors such as GAL4, bacterial proteins such as the repressor protein Lex A and mammalian transcription factors such as estrogen receptor.

The DNA binding domain within such proteins serves to bind the protein to the target sequence or "DNA binding protein recognition sequence" and therefore bring the protein to a set location within a DNA sequence.

One particular type of transcription factor binding site is named a "response element" which is a particular DNA sequence which causes a gene to respond to a regulatory transcription factor. Examples include the heat shock response element (HRE) and the glucocorticoid response element (GRE). A number of hormone response elements are also known to those skilled in the art. Response elements contain short consensus sequences which are the target or recognition for the DNA binding domains found within the corresponding inducible transcription factors such that, for example, transcription factors induced by a heat shock response bind ES, glucocorticoid-induced factors bind GREs etc. Other examples include the binding of estrogen receptor via a DNA binding domain to the specific DNA binding protein recognition sequence called the ERD or estrogen response domain. The interaction of transcription factors and response elements are described, for example in Genes VI, Lewin, Oxford University Press, 1997. Comparisons between the sequences of many transcription factors suggest that common types of motif can be found that are responsible for binding to DNA. Such motifs include the zinc finger motif, the helix-turn-helix or the helix-loop-helix. Other such motifs are known to the person skilled in the art.

The interaction between a DNA binding domain and a DNA binding protein recognition sequence can be used to direct mutation to a specific nucleic acid sequence. One way of directing mutation in this way is described as follows: an expression construct for expressing a fusion protein comprising Apobec with the estrogen receptor DNA binding domain (ERD) (Schwabe et al. Cell. 1993 Nov. 5; 75(3):567-78) is constructed as described below. The expression construct is expressed in yeast/E. Coli using standard transfection procedures. The yeast/E. Coli host cell is also engineered such that the desired target gene is also linked to a short ERD recognition sequence (Schwabe et al., 1993).

Screening for Modulators of AID Activity

Compounds having inhibitory, activating, or modulating activity can be identified using in vitro assays for activity and/or expression of AID or its homologues including APOBEC1, APOBEC 2, APOBEC 3c and APOBEC 3G, e.g., ligands, agonists, antagonists, and their homologs and mimetics.

Modulator screening may be performed by adding a putative modulator test compound to a cell expressing AID (or its homologues) in accordance with the invention, and monitoring the effect of the test compound on the function and/or expression of AID. A parallel sample which does not receive the test compound is also monitored as a control. The treated and untreated cells are then compared by any suitable phenotypic criteria, and in particular by comparing the mutator phenotype of the treated and untreated cells using methods as described herein.

The invention is further described below, for the purposes of illustration only, in the following examples.

EXAMPLES

Example 1

Figure 2:
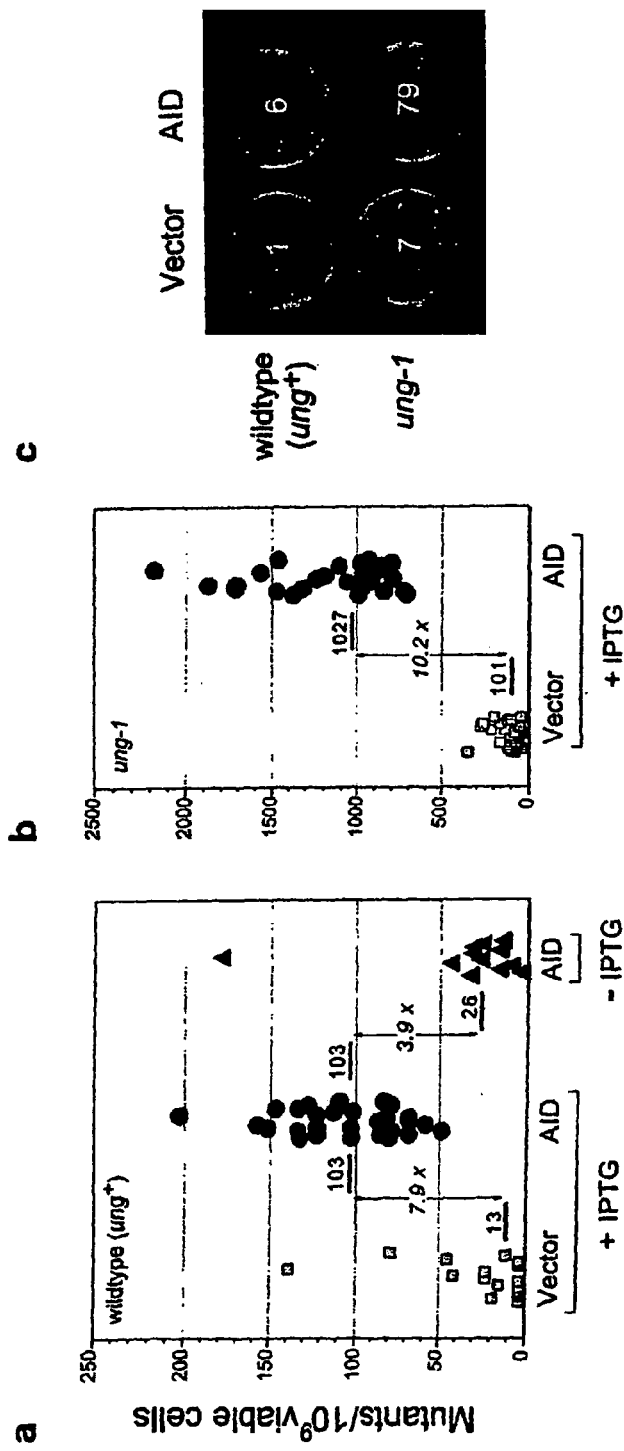

A plasmid containing a human AID cDNA expressed under control of the lac promoter was transformed into E. coli strain KL16 and its effect on the frequency of mutation to rifampicin-resistance ($Rif^R$) measured by fluctuation analysis (FIG. 2 and Table 1).

The AID expression plasmid was generated by cloning the human AID cDNA (Harris et al. (2002)) on an NcoI-HindIII fragment into pTrc99A (Pharmacia; gift of R. Savva). E. coli strains KL16 (Hfr(PO-45) relA1 spoT1 thi-1) and its ung-1 derivative (BW310) as well as AB1157 and its nfi-1::cat derivative (BW1161) were from B. Weiss; GM1003 (dcm-6 thr-1 hisG4 leuB6 rpsL ara-14 supE44 lacY1 tonA31 tsx-78 galK2 galE2 xyl-5 thi-1 mtl-1 mug::mini-Tn10) derivatives carrying ung-1 and/or mug::mini-Tn10 mutations were from A. Bhagwat.

APOBEC1 and APOBEC2 expression constructs were generated by subcloning the rat APOBEC1 cDNA (BamHI-SalI fragment of pSB20227 gift from N. Navaratrnan and J. Scott) or the human APOBEC2 cDNA (NcoI-BsaA1 fragment from IMAGE clones 341062). APOBEC3C was amplified from the Ramos human Burkitt lymphoma cell line cDNA using oligonucleotides 5' NNNGAATTCAAGGCT-GAACATGAATCCACAG (SEQ. ID. NO.: 1) and 5' NNNNNGTCGACGGAGACCCCTCACTGGAGA (SEQ. ID. NO.: 2). APOBEC3G was amplified from IMAGE clone 1284557 using oligonucleotides 5'-NNNGAATTCAAG-GATGAAGCCTCACTTCAGA (SEQ. ID. NO.: 3) and 5' NNGACTGCAGCCCATCCTTCAGTTTTCCTG (SEQ. ID. NO.: 4).

The E63A, W90S and C93A substitutions in APOBEC1 were introduced by site-directed mutagenesis using the following oligonucleotide pairs:

```
5'
ACCAACAAACACGTTGcAGTCAATTTCATAGAAA (SEQ ID NO.: 5)/
TTTCTATGAAATTGACTgCAACGTGTTTGTTGGT (SEQ ID NO.: 6),
```

-continued

5'ACCTGGTTCCTGTCCTcGAGTCCCTGTGGGGAG(SEQ ID NO.: 7)/
CTCCCCACAGGGACTCgAGGACAGGAACCAGGT,(SEQ ID NO.: 8)
and
CTGTCCTGGAGTCCCgcTGGGGAGTGCTCCAGG (SEQ ID NO.: 9)/
CCTGGAGCACTCCCCAgcGGGACTCCAGGACAG (SEQ ID NO.: 10)
(substitutions in lower case).

All constructs were verified by DNA sequencing and were identical to published sequences (Madsen et al. (1999), J. Invest. Dermatol. 113, 162-169; Jarmuz et al., Anant et al. (2001), Am. J. Physiol. Cell Physiol., 281, C1904-1916) or to existing GenBank entries (APOBEC1: NM_012907.1; APOBEC2: NM_006789.1).

The plasmids were transformed into E. coli strain KL16 and their effect on the frequency of mutation to rifampicin-resistance ($Rif^R$) measured by fluctuation analysis (Tables 2 and 3).

Mutation Assays

Mutation frequencies were measured by determining the median number of colony-forming cells surviving selection per $10^9$ viable cells plated. Each median was determined from 8-16 independent cultures grown overnight to saturation in rich medium supplemented with 100 µg/mL carbenicillin and 1 mM IPTG (unless indicated otherwise). $Rif^R$ and $Nal^R$ colonies were selected on rich medium containing 100 µg/ml rifampicin and 40 µg/ml nalidixic acid respectively. Valine- and fucose-resistant mutants were selected on minimal M9 medium containing 0.2% glucose/40 µg/ml L-Valine and 0.1% L-arabinose/0.2% D-fucose respectively.

In multiple experiments performed in the presence of the transcriptional inducer IPTG, the AID-transformed cells generated $Rif^R$ colonies at a frequency some 4-8 fold higher than vector-transformed controls. This stimulation was evident in different genetic backgrounds (KL16, GM1003 and AB1157), was dependent upon AID (monitored±IPTG) and was not peculiar to the selection applied, being also clear when mutation to nalidixic acid (Nal)-, valine- or fucose-resistance was monitored (FIG. 2 and Table 1). The variation in the mutation enhancement observed in the different selections could reflect differences in the types and abundances of mutations that confer resistance.

In similar multiple experiments, cells transformed with Apobec-1 generated $Rif^R$ colonies at a much higher frequency (several hundred fold) than vector-transformed controls. Cells transformed with other Apobec homologues, Apobec3C and Apobec3G, also showed an increased frequency (10-20 fold) of mutation to $Rif^R$ compared to the vector-transformed controls.

Figure 5:
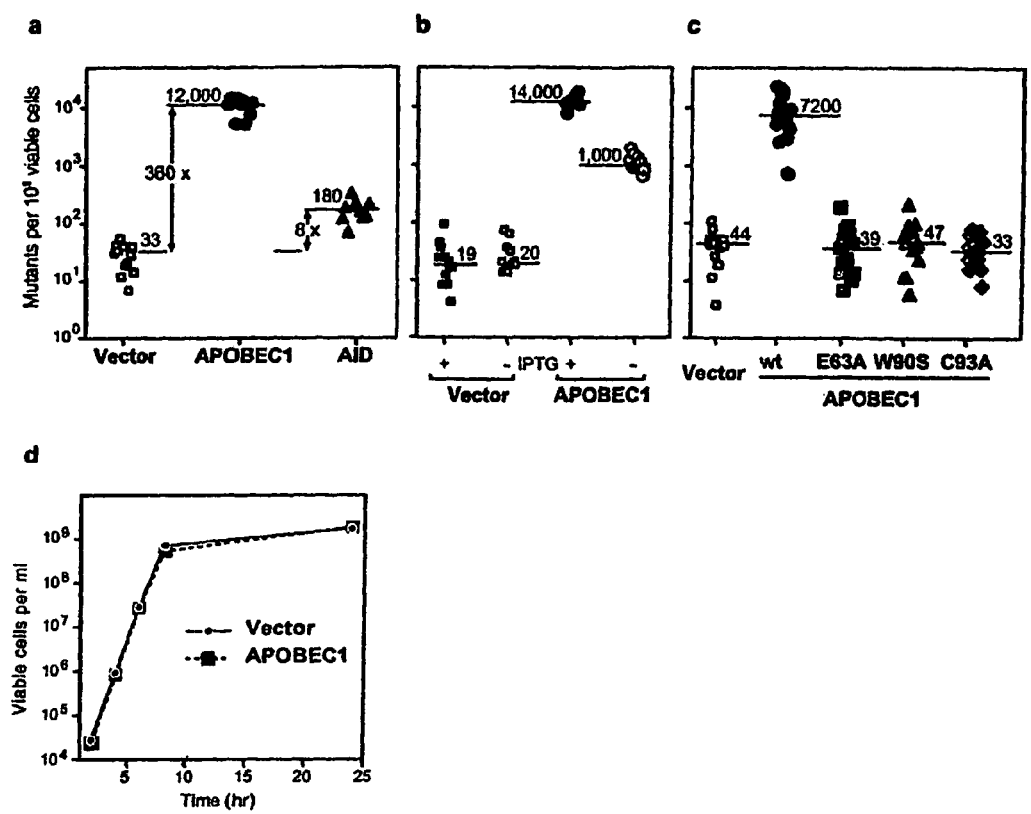

For the experiments shown in FIG. 5 and Table 3, all measurements were performed using KL16 or its ung-1 derivative BW310 transformed with vector alone or an expression construct as indicated. Mutation frequencies were measured by determining the median number of colony-forming cells surviving selection per $10^9$ viable cells plated. Each median presented in FIG. 5 and Table 3 was determined from 12-16 independent cultures grown overnight to saturation in rich medium supplemented with 100 µg/ml carbenicillin and 1 mM IPTG (with the exception of control experiments in which the inducer IPTG was omitted, FIG. 5b). IPTG-induced expression of APOBEC1 or its homologues conferred no obvious defect in cell growth or viability (e.g. APOBEC1, FIG. 5c). $Rif^R$ mutants were selected on rich medium containing 100 µg/ml rifampicin and sequenced.

Only about 1% of the $Rif^R$ colonies failed to contain mutations in the region of rpoB sequenced [nucleotides 1525-1722, numbering from the initiating ATG; GenBank AE000472].

The nature of the $Rif^R$ and $Nal^R$ mutants was determined by directly amplifying and sequencing the relevant section of the rpoB [627 by PCR product amplified using 5' TTGGC-GAAATGGCGGAAAACC (SEQ. ID. NO.: 11) and 5'-CAC-CGACGGATACCACCTGCTG (SEQ. ID. NO.: 12)] or gyrA [521 by PCR product amplified using oligonucleotides 5'-GCGCGGCTGTGTTATAATTT (SEQ. ID. NO.: 13) and 5' TTCCGTGCCGTCATAGTTATC (SEQ. ID. NO.: 14)].

Figure 3:
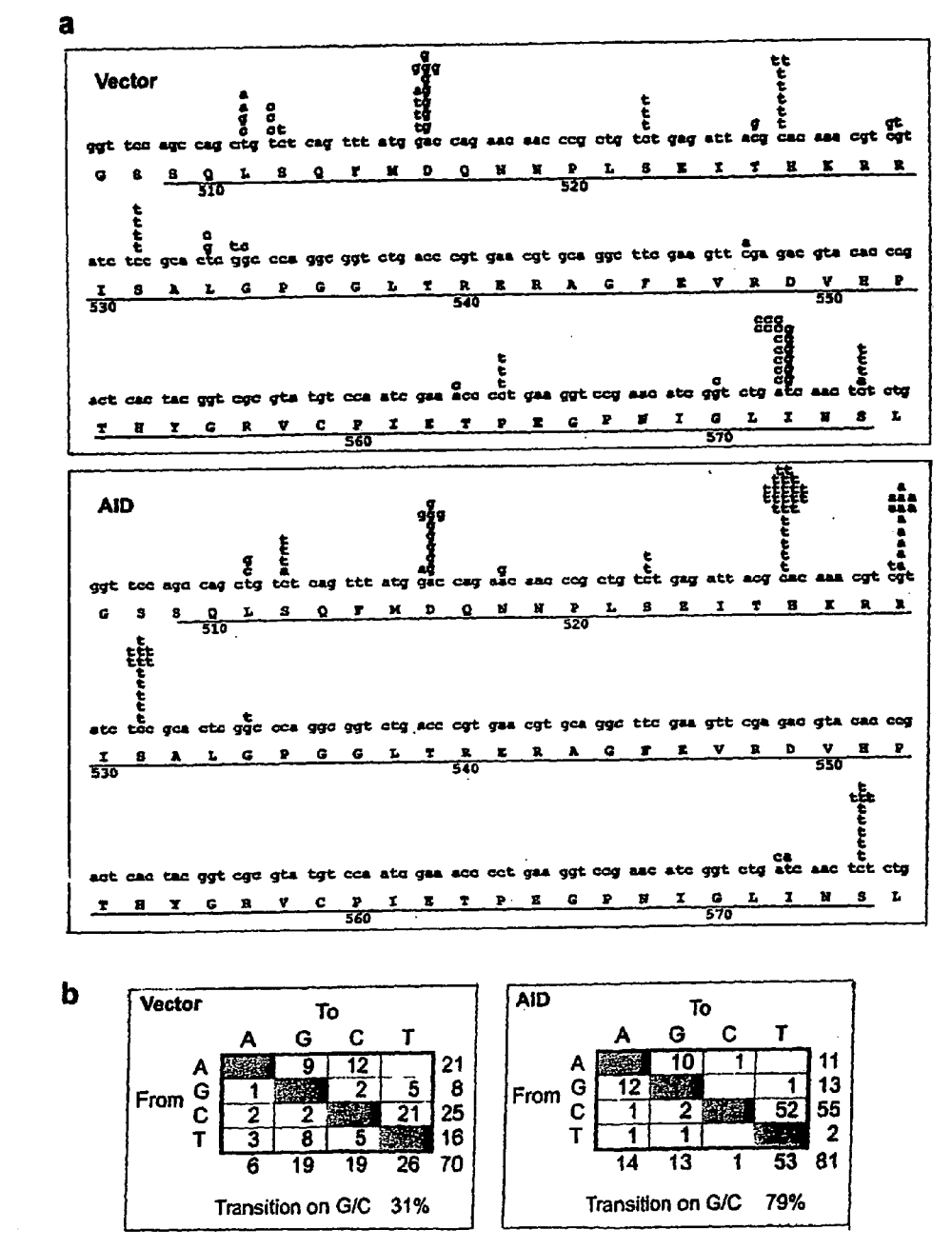
Figure 4:
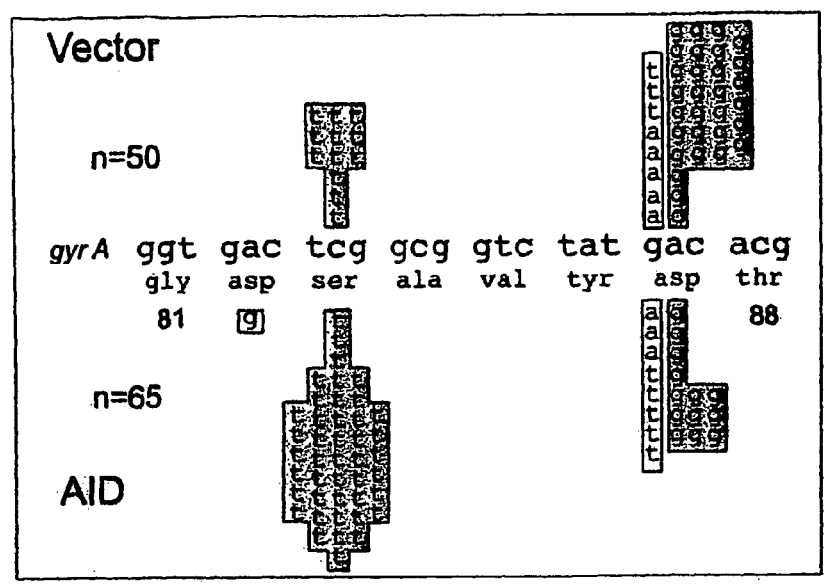

If the AID-mediated enhancement in mutation frequency is due to a stimulation of dC deamination, the pattern of mutation to $Rif^R$ should show a shift toward dC→dT and dG→d transitions. Sequence of the rpoB gene in multiple independent $Rif^R$ colonies, revealed that this is indeed the case. Such transitions account for 79% of the mutations scored in the AID-transformed cells but only for 31% of the mutations in the vector transformed controls (FIG. 3a, b). Given the extent of mutation stimulation by AID, the data are consistent with the entire AID-mediated enhancement being due to transitions at dG/dC. A similar conclusion was obtained by examining the spectrum of gyrA mutations in the $Nal^R$ colonies—despite the fact that the selected mutations appeared restricted to essentially three nucleotide positions. Thus, whereas 34% of the gyrA mutations amongst the control transformants are nucleotide transitions at dG/dC, the percentage increases to 71% in the AID transformants (FIG. 4)

It is notable that there is a striking difference in mutation distribution between the AID transformants and controls. Analysis of the rpoB mutations amongst the vector-transformed control cells reveals that dC→dT transitions at positions Ser512, Ser522, His526, Se531, Pro564 and Ser574 can all confer $Rif^R$. However, transitions at only some of these positions (His526, Ser531 and Ser574) are enhanced amongst the AID transformants whereas other positions (Ser522 and Pro564) show little sign of increased mutation. Even more striking is the fact that a common dG→dA transition in the AID transformants (Arg529) is not seen at all in the controls (FIG. 3). Similar evidence of specific targeting comes from gyrA. Whereas dC→dT transitions at Ser83 and dG→dA transitions at Asp87 can both confer $Nal^R$, it is the COT transitions at Ser83 that are selectively enhanced by AID (FIG. 4). Despite this strong evidence that AID-dependent mutation is non-random, presumably depending upon local sequence environment, we cannot discriminate on these datasets whether this sequence preference reflects a hotspot preference similar to that of the dG/dC-biased phase antibody hypermutation (Rada et al. (1998)) since there are only a limited number of base substitutions that can yield the selected phenotypes.

If AID-induced mutations in the E. coli transformants are indeed occurring through deamination of dC, an enhancement of the effect would be expected in cells lacking uracil-DNA glycosylase (UDG). This is indeed the case. Although both UDG deficiency and ectopic expression of AID are sufficient in themselves to yield a mutator phenotype, AID expression in an ung⁻ background yielded a mutation frequency that was much greater than the sum of their independent mutation frequencies (FIG. 2 and Table 1). A similar effect was seen in E. coli expressing Apobec-1 (see Table 2).

In E. coli ung-1 mutants, some back-up uracil DNA-glycosylase activity may be provided by the product of the mug gene (Sung et al. (2001) and Mokkapati et al. (2001)). It is found that whilst the AID mutator effect is not significantly higher in a mug⁻ than mug⁺ background, the mug mutation allows at most a slightly augmented AID-mutator effect when combined with ung-1 (Table 1). If AID were to act by deaminating dG rather than dC, an increased mutation frequency in a background deficient in endonuclease V (encoded by nfi) might be anticipated since this enzyme is implicated in the repair of deoxyxanthosine[21,22]. This does not occur; the mutation frequency displayed by AID-transformed nfi-1 cells approximates the sum of the frequencies that are independently attributable to AID and nfi-1 (Table 1).

The data strongly suggest that AID mediates the deamination of dC residues in the DNA. The homology of AID to Apobec-1 and cytidine deaminases (Muramatsu et al (1999)) obviously argues in favour of a close involvement of AID in the DNA deamination process itself. The preferential targeting of mutation to the immunoglobulin loci in lymphocytes presumably depends on proteins with which AID associates. Given that the cis-regulation of both switch recombination and hypermutation is linked to the transcription regulatory elements (Manis et al. (2002); Betz et al (1994)), it would appear likely that AID is recruited either directly or indirectly by transcription- or chromatin-associated factors.

APOBEC1-transformed bacteria grown in the presence of the transcriptional inducer IPTG displayed massively elevated frequencies of $Rif^R$ mutation (FIG. 5a). This enhancement was confirmed by fluctuation analyses of $Rif^R$ mutants observed in three independent experiments (Table 3 top). In comparison to vector-transformed cells, the median enhancement by APOBEC1 ranged from 440- to 700-fold (mean of 530), whereas that attributable to AID ranged from 3.8 to 13-fold (mean of 7.8 in agreement with data above). The observed increases were due to APOBEC1 since experiments performed in the absence of the inducer IPTG resulted in a significantly diminished effect (FIG. 5b). Furthermore, single amino acid changes E63A, W90S and C93A (which are located at or close to the proposed $Zn^{2+}$-coordination domain at the active site of APOBEC1 (Navaratnam et al) abolished the enhancement (FIG. 5c). The stimulation was not specific to the selection or the locus ($Rif^R$ mutations map largely to the rpoB gene since it was also clear when resistance to nalidixic acid was selected (due mostly to mutations in the gyrA gene) (Table 3 (top)). Mutation frequencies at gyrA were significantly lower than at rpoB; this likely reflects restrictions in numbers of base substitutions that each locus permits (both genes are essential and fewer sites appear mutable in gyrA). It is notable that whilst APOBEC1 yields a mutator phenotype in these assays as strong as that achieved with some of the most potent *E. coli* mutators (e.g. mismatch repair-defective strains (Schapper (1993), J. Bio. Chem. 268, 23762-23765)), the increased mutation load due to APOBEC1 expression caused no obvious defects in cell growth or viability (FIG. 5d). This might reflect the nature of the lesions introduced by APOBEC1 expression.

If, like AID, the observed stimulation of mutation is due to increased dC deamination, then this should be apparent in the spectrum of $Rif^R$ mutations—a bias toward dC/dG→dT/dA transition mutations would result. This was confirmed by sequencing rpoB gene PCR products from purified $Rif^R$ colonies selected from APOBEC1-transformed cultures (as well as from AID-transformed and vector-transformed controls). By comparison with vector-transformed controls, APOBEC1-transformed cells showed a dramatic shift in mutation spectrum, from 27% (32/120 mutations) to 100% (136/136 mutations) transition mutations at dC/dG (FIG. 2). Consistent with the results presented above, AID-transformed *E. coli* gave a somewhat less dramatic shift to 82% (102/124) transitions at dC/dG (FIG. 7) reflecting the fact that AID, at least in this system, is a less potent mutator than APOBEC1.

Figure 7:
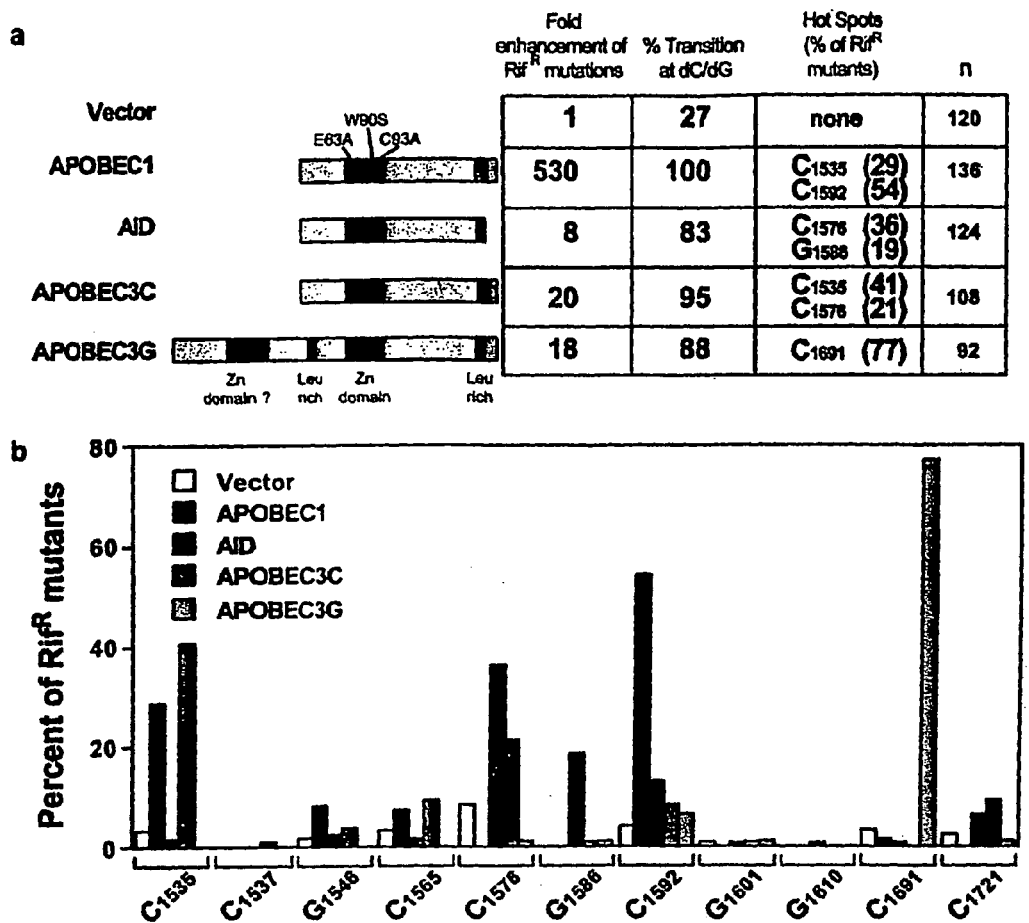

The mutation spectra revealed string local differences between vector-, APOBEC1- and AID-transformed cells with respect to the specific dC/dG pairs targeted. Whereas, in keeping with AID, the majority of dC/dG to dT/dA transitions in rpoB in AID-transformed cells clustered at C1576 (45/124 mutations) and G1586 (23/124 mutations), those in APOBEC1-transformed cells showed a quite distinct distribution with major hotspots at C1535 (39/136 mutations) and C1592 (74/136 mutations) (FIG. 6a and FIG. 7). Thus, the entire enhancement of $Rif^R$ mutation frequency observed in APOBEC1-transformed cells occurs via transitions at dC/dG base pairs but with the local targeting specificity being remarkably different from that of AID.

The different local targeting specificities of APOBEC1 and AID strongly argues that both proteins are involved in a dC deamination process, generating dU/dG lesions in DNA. Given this likely mode of action, one would expect that the stimulation of mutation by APOBEC1 (like that by AID) would be enhanced in cells lacking uracil-DNA glycosylase (UDG), an enzyme that specifically recognises dU in DNA and initiates base excision repair of dU/dG lesions (Lindahl). UDG-deficiency (ung-1) and APOBEC1 expression by themselves enhance mutation about 10- and 500-fold, respectively. APOBEC1 expression in UDG-deficient cells further increases levels of mutation to about 2600-fold above vector-transformed $ung^+$ cells, a much more than additive effect demonstrating that APOBEC1 is capable of triggering dU/dG lesions (Table 3 top). Despite the additional mutation load in ung-1 cells, sequence analysis of the mutations conferring $Rif^R$ revealed that, as for AID, the mutational targeting by APOBEC1 in an ung-1 background was essentially the same as in $ung^+$ cells (data not shown).

At least six other APOBEC1-like proteins exist in humans (Madsen et al; Jarmuz et al; Anant et al). APOBEC2 (also called APOBEC1-related cytidine deaminase-1, ARCD-1) is found on chromosome 6p21.1 and the others, termed APOBEC3A through APOBEC3G (also termed phorbolins or ARCDs) are encoded on chromosome 22q12-q13. They all contain a region homologous to the putative $Zn^{2+}$-binding cytidine deaminase motif of APOBEC1. This suggested that the mutator activities of these proteins might also be conserved and prompted us to ask whether these homologues might also work on DNA. Expression of APOBEC3C and APOBEC3G, representative members of the chromosome 22 cluster (FIG. 7a), but not APOBEC2, triggered increases in the frequencies of mutation to $Rif^R$ and $Nal^R$ in *E. coli* (Table 3 bottom). The stimulation of mutation by APOBEC3G is significantly greater when monitored by the frequency of $Rif^R$ rather than $Nal^R$ clones (Table 3). This may reflect the relatively strong target preference of APOBEC3G (see below) taken together with the fact that there are many more dC/dG targets in rpoB than in gyrA that can confer resistance to the relevant antibiotic. The mutation frequencies to $Rif^R$ achieved with both APOBEC3C and APOBEC3G was also further elevated in an ung-1 background indicating that they, like APOBEC1 and AID, potentiate dU/dG mispairs, substrates for UDG and subsequent repair (Lindahl). In contrast, cells transformed with a human APOBEC2 expression construct showed neither increased mutation frequencies ($ung^+$ or $ung^-$ backgrounds; Table 3 bottom) nor a significantly altered rpoB mutation spectrum (data not shown).

That APOBEC3C and APOBEC3G also act like APOBEC1 and AID is supported further by a near complete shift in the spectrum of mutations that yield $Rif^R$, from 27%

(32/120) dC/dG→dT/dk transitions in vector-transformed cells to 94% (102/108) and 88% (81/92) in APOBEC3C- and APOBEC3G-transformed cells respectively (FIG. 7). Moreover, a direct comparison of the dC/dG base pairs targeted by APOBEC3C and APOBEC3G with those targeted by APOBEC1 and AID revealed obvious biases, the most striking of which was mutation of C1691 by APOBEC3G (71/92 mutations compared to 4/120 for vector-transformed cells). APOBEC3C, on the other hand, shared one hotspot with APOBEC1 (44/108 at C1535) and another with AID (23/108 at C1576), and appeared to be slightly more promiscuous causing dC/dG→dT/dA transition mutations at eight positions in rpoB FIG. 7b).

Example 2

APOBEC1 Expressed in *E. coli* can be Used to Mutate a Heterologous Gene Integrated into the Chromosome The *Bacillus subtilis* gene SacB is toxic to *E. coli* in the presence of sucrose. SacB is cloned under the control of the *E. coli* promoter for PhoB and the cassette integrated into the chromosome of *E. coli* strain DH10b at the Lambda phage attachment site using pRB700 (FIG. 8a), a derivative of the CRIM system plasmid pSK50Δ-uidA2 (Haldimann et al 1996 Proc Natl Acad Sci USA. 93(25):14361-6, Haldimann and Wanner 2001 J. Bacteriol. 183(21):6384-93). The PhoB promoter is active under conditions of low inorganic phosphate availability. Thus mutants in the SacB cassette can be selected by growing independent colonies transfected with either an APOBEC-1 expression construct or a control plasmid to saturation (using one fortieth of the colony as the inoculum) and plating on minimal MOPS medium containing 5% sucrose and limiting phosphate.

PCR and subsequent sequencing of the integrated SacB genes in these sucrose resistant colonies demonstrates that spontaneous mutants at this locus arise primarily by transposon insertion (and therefore generate a significantly larger than expected PCR product). This accounted for 13/16 spontaneous mutations. In contrast, point mutations predominate when APOBEC-1 is expressed. Furthermore, these point mutations are overwhelmingly (32/33) transitions at C and G, consistent with these mutations arising by deamination of dC as expected (FIG. 9).

Enhanced Targeting of Mutation can be Achieved by Inducing Convergent Promoters Upstream and Downstream of the Desired Gene.

The dependence of mutation caused by APOBEC-1 at this locus on transcription is investigated. APOBEC-1 increases the mutation frequency at SacB approximately 12-fold when colonies are grown in rich medium, and growth in medium containing limiting phosphate does not appear to enhance mutation at this locus. To investigate the possibility that transcription in both directions might be required to show an increase in mutation frequency, a variant SacB cassette in pRB740 is created, under the control of the same PhoB promoter, additionally placing the strong IPTG inducible Trc promoter downstream of the SacB gene in the opposite orientation (FIG. 8b).

The mutation frequency following growth in rich medium with IPTG of SacB in this case is comparable to that of the original cassette without the convergently orientated Trc promoter, and so is the spectrum of point mutations obtained (20/20 are transitions at C or G), indicating that this variant SacB cassette does not mutate with an appreciably higher frequency when transcription is induced only in the antisense direction.

Figure 10A:
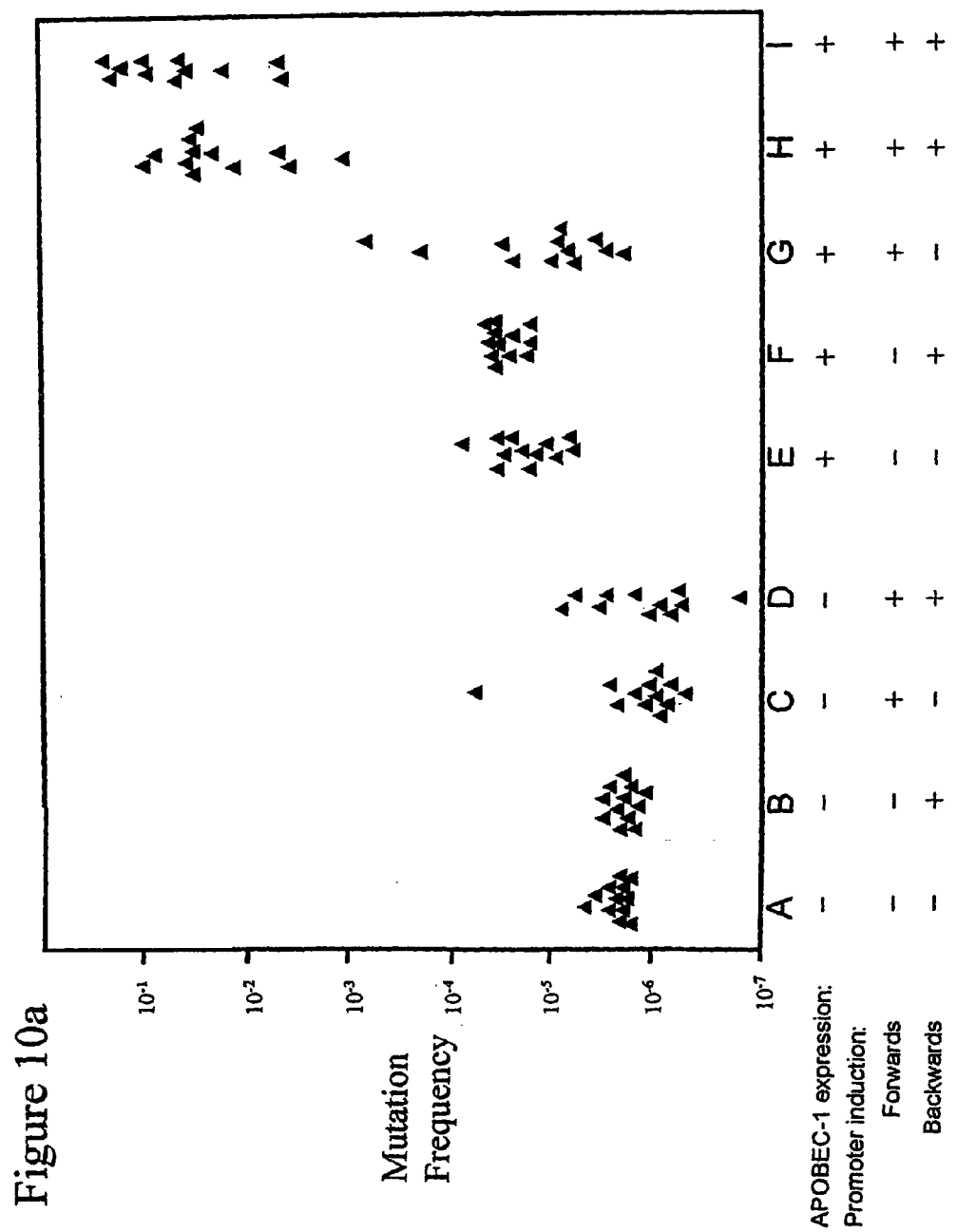
FIG. 10a shows mutation frequency in constructs when transcription is induced in either or both directions.

However, following growth in limiting phosphate together with IPTG, the mutation frequency is enhanced approximately 1000 fold above that achieved either by APOBEC-1 without the downstream promoter under the same conditions, or with the downstream promoter in rich medium (FIG. 10a, b).

Thus, activation of convergent promoters located on opposite sides of the gene is able to enhance APOBEC-1 induced mutation at that locus very appreciably. Furthermore, expression of the less mutagenic APOBEC family members AID and APOBEC-3G under these conditions of convergent transcription also gives rise to a significant increase in mutation frequency above background and a shift towards the expected PCR product size, indicating that transposon insertions are responsible for a lower proportion of the observed mutants. The expected PCR size product is obtained in 10/10 and 7/10 cases for AID and APOBEC3G respectively, compared to only 2/10 and 5/10 respectively under non-transcribing conditions (FIG. 11).

Under conditions of bi-directional transcription, transitions at C or G account for 8/8 and 5/5 of the point mutations observed for AID and APOBEC3G respectively (FIG. 11). Taken together, these results demonstrate that targeted deamination by members of the APOBEC family can be achieved if the desired gene to be targeted is placed between convergent promoters (FIG. 11).

Example 3

Deamination of Cytosine to Uracil in DNA can be Achieved in Vitro Using Partially Purified APOBEC1 from Extracts of Transformed *Escherichia coli*

Plasmids and Bacteria

The pTrc99- and pET-based expression vectors for rat APOBEC1 and its E63→A mutant, for human APOBEC2 and for *E. coli* dCTP deaminase as well as the *E. coli* host strains have been described previously (Rada et al. (2002) *Curr. Biology* 12, 1748-1755, Randerath K., and Randerath E. (1967) *Method Enzymol.* 12, 323-347). The pTrc99- and pET-based vectors differ both in the nature of the promoter used (pTrc99 uses the trp/lac hybrid promoter whereas pET uses the T7 promoter) and in the length of heterologous peptide linked to the amino-terminus of the recombinant protein (9 amino acid with pTrc99 but 34 amino acid with pET (Rada et al. (2002) *Curr. Biology* 12, 1748-1755, Randerath K., and Randerath E. (1967) *Method Enzymol.* 12, 323-347)).

Oligodeoxyribonucleotides

The oligodeoxyribonucleotides used are listed in Table 4.

Preparation of Recombinant APOBEC1

A 2 ml overnight culture of a fresh *E. coli* transformant grown in LB, 0.2% Glucose, 50 µg/ml carbenicillin was diluted into 300 ml of the same medium and grown at 37° C. to an $A_{600}$ of 0.8. The culture was chilled on ice for 20 min and then incubated with aeration for 16 h at 16° C. in the presence of inducer (1 mM IPTG). Cells were harvested by centrifugation, washed and resuspended in 20 ml H buffer (50 mM Tris.HCl, pH7.4, 50 µM KCl, 5 mM EDTA, 1 mM DTT and a protease inhibitor cocktail [Roche]).

Following sonication and ultracentrifugation (100,000 g for 45 min), the supernatant was passed through a 0.2 µm filter and applied to a Sepharose Fast-Flow Mono-Q column (Amersham Biosciences; 10 ml bed volume). After washing with seven column volumes of buffer H, bound proteins were eluted in buffer H supplemented with increasing salt concentrations (from 50 to 1500 mM Cl$^-$) collecting 15 ml fractions. Fractions and flow-through were concentrated one-hundred fold using VivaSpin concentrators ($M_r$ 10,000 cut-off) (VivaScience) and assayed. Samples eluting with 1000-1500 mM salt were pooled and loaded in a volume of 0.5 ml onto a HighPrep Sephacryl S-200 High-Resolution 16/60 gel-filtration column (Amersham Biosciences) in buffer H. Fractions (1 ml) were collected and concentrated twenty fold before analysis.

TLC-Based Deaminase Assay

Samples (2-4 µl) were incubated at 37° C. for 5 h in 20 µl of buffer R (40 mM Tris pH 8, 40 mM KCl, 50 mM NaCl, 5 mM EDTA, 1 mM DTT, 10% glycerol) containing 75,000 cpm of α-[$^{32}$P]dC-labelled single-stranded DNA (prepared by a 3 min heating to 95° C. of the products of asymmetric PCR amplification of the lacI region in pTrc99 performed using α-[$^{32}$P]dCTP (3000 Ci/mmol)). Following phenol extraction and ethanol precipitation, the DNA was digested with *Penicillium citrinum* P1 nuclease (Sigma) overnight at 37° C. (Grunau C., Clark S. J., and Rosenthal A. (2001) *Nucleic Acids Res.* 29, E65) and the P1 digests then subjected to thin layer chromatography on PEI-cellulose in either (i) 0.5 M LiCl at 4° C. or (ii) at room temperate in 1 M CH$_3$COOH until the buffer front had migrated 2.5 cm and then in 0.9 M CH$_3$COOH:0.3M LiCl (Cohen, R. M., and Wolfenden, R. (1971) *J. Biol. Chem.* 246, 7561-7565). Products were detected using a phosphorimager. Chemical deamination of cytosine in DNA using bisulfite/hydroquinone was performed as described (Yamanaka et al. (1995) Proc. Nat Acad. Sci. USA, 92, 8483-8487).

UDG-Based Deaminase Assay

Samples (1-2 µl) were incubated at 37° C. for 2 h in 10 µl of buffer R with 5'-biotinylated oligonucleotides that either were synthesized with fluorescein at their 3'-ends (3 pmol of oligonucleotide per reaction) or were 3'-labelled by ligation with α-[$^{32}$P]dideoxyadenylate (100,000 cpm; 0.1 pmol) using terminal deoxynucleotidyl transferase.

Reactions were terminated by heating to 90° C. for 3 min and oligonucleotides purified on streptavidin magnetic beads (Dynal), washing at 72° C. (except in FIG. 2A, where the streptavidin purification step was omitted). Deamination of cytosine in the oligonucleotides was monitored by incubating the bead-immobilised oligonucleotides at 37° C. for 30 min with excess uracil-DNA glycosylase (0.5 units UDG; enzyme and buffer from NEB) and then bringing the sample to 0.15M in NaOH and incubating for a further 30 min. The oligonucleotides were then subjected to electrophoresis on 15% PAGE-urea gels which were developed by either fluorescence detection or phosphorimager analysis.

Western Blotting

Western blot detection of APOBEC1 following SDS/PAGE of samples that had been diluted 20-100 fold was performed using a goat-anti-APOBEC1 serum (Santa Cruz Biotechnology), developing with horseradish peroxidase-conjugated donkey anti-goat immunoglobulin antiserum (Binding Site, Bilin, UK). Low-range molecular weight markers were from BioRad.

Results

DNA Deamination Assay in Cell Extracts

Since, of all the APOBEC1 family members tested, APOBEC1 displayed the most potent mutator activity in the *E. coli* mutation assay (Randerath K and Randerath E. (1967) Method Enzymol 12, 323-347), APOBEC1-transformed *E. coli* were investigated in order to see if DNA deamination activity in vitro using cell extracts could be detected.

Initially, the UDG-based deaminase assay was tried, working with an oligodeoxyribonucleotide substrate. However, no evidence of deamination was obtained using double-stranded oligonucleotide substrates whereas single-stranded oligonucleotides were rapidly degraded by both APOBEC1 and control extracts (data not shown). The possibility that the DNA deaminating activity might be specific for single-stranded substrates but that this activity might be masked by non-specific nucleases was investigated. An assay that would be less sensitive to contaminating nucleases (FIG. 12A) was devised.

The bacterial extracts were incubated with α-[$^{32}$P]dC-labelled single-stranded DNA which was then purified, digested with nuclease P1 and subjected to thin-layer chromatography to test for the presence of α[$^{32}$P]dUMP. Clear evidence of dC deamination in this assay was detected using extracts of *E. coli* expressing two different APOBEC1 constructs but not from control extracts or from extracts made from *E. coli* cells carrying plasmids expressing mutant APOBEC1, APOBEC2 or dCTP deaminase (none of which function as DNA mutators in the bacterial assay (Randerath K and Randerath E. (1967) Method Enzymol 12, 323-347)) (FIG. 12B). The DNA deaminase activity was evident in APOBEC1-transformants of a mutant *E. coli* deficient in both dcd-mad cdd-encoded deaminases (FIG. 12B (iii)). That the product of APOBEC1 action was indeed dUMP is indicated by the co-migration of the radioactive product with dUMP in two distinct buffer systems.

These results suggested fractionation of the extracts of APOBEC1-transformed *E. coli* to see if the DNA deamination activity could be sufficiently separated from non-specific nucleases so as to be detectable using the oligonucleotide cleavage assay.

Partial Purification

Pilot experiments revealed that ion-exchange chromatography could be used to obtain samples of APOBEC1 that contained diminished non-specific nuclease activity. Thus, whilst only a proportion of the APOBEC1 polypeptide bound to the Mono-Q column (around 10-20% based on ECL quantitation of the Western blot assay), elution of this bound fraction with >0.8 M Cl$^-$ yielded a sample that displayed cytosine-DNA deamination activity (as monitored using the TLC-based assay) but containing diminished non-specific nuclease activity in the UDG-based assay (FIG. 13A). These fractions were then concentrated and subjected to gel filtration (FIG. 13B). The major APOBEC1 peak eluted in fractions 0.7-9 (corresponding to an $M_r$ of 95-140,000) co-eluting with peak DNA deaminating activity. Indeed, with these fractions from the gel filtration column, DNA deamination could now readily be detected by the UDG-based assay using a single-stranded oligonucleotide substrate (although the peak fractions also contained activity that removed the 3'-label from the oligonucleotide). Mass spectrometric analysis of proteins in fraction 9 following SDS/PAGE revealed the recombinant APOBEC1 migrating at the position marked by the asterisked in FIG. 13B(i) although the majority of the bands derived from ribosomal proteins.

Characteristics of the DNA Deaminating Activity

The UDG-based deaminase assay was used to monitor the specificity and characteristics of the partially purified APOBEC1 (FIG. 14A). Samples were incubated with a single-stranded oligodeoxyribonucleotide (with or without its complement) which contained internal dC residue(s) and that was 5'-biotinylated as well as 3'-labelled. After purification on streptavidin, the oligonucleotide was treated with UDG (plus alkali), resulting in site-specific cleavage if the oligonucleotide had been subjected to dC→dU deamination. Thus, deamination is read out by the appearance of the specific cleavage product following PAGE-urea analysis.

The partially-purified wild type protein (but not the E63→A mutant) showed clear activity on a single-stranded oligonucleotide with the cleavage being dependent on the subsequent incubation with UDG (FIG. 14B, C). The deaminating activity was not inhibited by tetrahydrouidine (which inhibits cytidine deaminases (Frederico et al. (1990) Biochemistry, 29, 2532-2537)) or by RNAse (FIG. 14D). Strikingly [and consistent with our inability to detect deamination on double-stranded oligonucleotide substrates using crude extracts of bacterial transformants (see above)], the activity was blocked if a complementary (but not if an irrelevant) oligonucleotide was titrated into the assay (FIG. 14E). Examination of the cleavage products generated in the UDG-based assay suggests that not all dC residues are equally susceptible to APOBEC1-mediated deamination. It is clear, for example, that in oligonucleotide SPM168 the third cytosine in the sequence TCCGCG is much less favoured than the other two (FIG. 14B-E). Similarly, evidence of specificity comes from comparing various related oligonucleotides as substrates, where all the data taken together point to deamination being especially disfavoured when a purine is located immediately-5' of the cytosine (FIG. 14F, G).

Discussion

The results described here provide biochemical evidence that APOBEC1-mediated deamination of cytosine to uracil can occur on single-stranded DNA, is dependent on local sequence context and is abolished by mutation of the APOBEC1 zinc-coordination motif. Unlike AID (where genetic evidence indicates that the natural physiological substrate of deamination is DNA (Harris et al. (2002) Mol. Cell 10, 1247-1253, Wagner et al. (1989) Proc. Nat. Acad. Sci. USA, 86, 2647-2651), the major physiological substrate of APOBEC1 is clearly apolipoprotein B RNA (Teng et al. (1993) Science 260, 1816-1819, Blanc, V. and Davidson, N. O. (2003) J. Biol. Chem. 278, 1395-1398). Nevertheless, the observation that misexpression of APOBEC1 in transgenic mice predisposes to cancer suggests that APOBEC1-mediated DNA deamination could well be of pathological relevance.

Given the abundance of APOBEC1 polypeptide in the peak fraction from the gel filtration column, it appears that—on average—each molecule of recombinant APOBEC1 is responsible for in the order of a single deamination event in a 10 minute incubation in the UDG-based assay. Crude calculations indicate that if the ~500 molecules of APOBEC1 expressed in each *E. coli* transformant displayed a DNA deamination activity of this order in vivo and if this were targeted randomly to all cytosine residues in the genome, then this could, in principle, be more than sufficient to account for the several thousand-fold enhanced mutation frequencies seen at the rpoB and other loci in UDG-deficient *E. coli* following 20 generations of growth (Randerath K. and Randerath E. (1967) Method Enzymol 12, 323-347). Similarly, somatic hypermutation of immunoglobulin variable genes by targeted AID-mediated dC deamination may involve a single and most probably less than ten targeted dC deamination events in each B lymphocyte cell cycle.

The results provide information about the preferred target of APOBEC1-mediated DNA deamination. The in vitro assay reveals a clear sensitivity to the local sequence context of the dC residue to be deaminated. The results obtained here suggest there may be bias against a 5'-flanking purine residue. This would accord well with the in vivo data where a near-total restriction to mutation at dC residues with a 5'-flanking pyrimidine is seen at the rpoB locus (Randerath and Randerath).

The in vitro assay also reveals that APOBEC1 deamination is targeted to single-stranded DNA and, indeed, was undetectable on double-stranded DNA. This specificity for single-stranded DNA is in accordance with the fact that the natural substrate of APOBEC1 is most likely single-stranded RNA (Blanc and Davidson) and, presumably, the same active site in APOBEC1 is used for both types of polynucleotide. Furthermore, spontaneous deamination of cytosine is also much more rapid in single- (as opposed to double-) stranded DNA which may explain the correlation with transcription of the DNA target gene described herein and where convergent promoters increase the availability of single-stranded DNA to APOBEC1.

Example 4

Expression of Apobec-1 Fusion Proteins

The Apobec-1 expression plasmid was generated as described above but a nucleic acid encoding rat Apobec1 with an aminoterminal fusion encoding:

Met-His-His-His-His-His-His-His-His-Tyr-Asp-Ile-

Pro-Thr-Ala-Ser-Glu-Asn-Leu-Tyr-Phe-Gln-Gly-Ser- (SEQ ID NO.: 15) joining to the initiator Met of Apobeo-1

The expression construct was expressed from in *E. coli* strain BL21 DE3 (purchased from Novagen) and the effect on the frequency of mutation to rifampicin-resistance ($Rif^R$) measured by fluctuation analysis as described above.
The results are as follows:
RifR Colonies

| vector alone | 42 | 35 | 28 | 23 |
|---|---|---|---|---|
| His-Apobec-1 | 3000 | 3000 | 2000 | 1500 |

(The numbers are numbers of Rifr colonies in 4 independent experiments, the experiments being performed as in Tables 1 and 2).

This demonstrates that the Apobec fusion protein with a His-tag fused to His-N-terminus retains mutator activity in *E. coli*.

Example 5

Hybridisation Experiments

A cancer profiling array was obtained from Clontech (Cat. No. 7757-1) and hybridised as directed with the following $^{32}$P-dCTP-labeled human cDNA probes: APOBEC1 (IMAGE clone 2107422), APOBEC3G (IMAGE clone 1284557)

and ubiquitin (control provided with array). The array was hybridised first with APOBEC1, subsequently with APOBEC3G, and finally with ubiquitin. After each hybridisation the probe was removed by boiling in 0.5% SDS. Hybridisation images, shown in FIG. 15, were visualised with the Typhoon Phosphoimaging System (Pharmacia) and ImageQuant software. Data are grouped by tissue to facilitate comparison, although the entire blot (representing all tissues shown) was hybridised simultaneously as a single filter in each experiment (i.e. with each probe) and the autoradiographic image subsequently separated by computer manipulation (without adjusting gain or background).

Results

APOBEC1 expression appears to be restricted to gastrointestinal tissues (colon, stomach, rectum, and small intestine), whereas APOBEC3G was expressed to some extent in all tissues examined. Perhaps most notable is the fact that for some tumour samples, APOBEC1 (colon and rectum) and APOBEC3G (breast and kidney) appear better expressed than in corresponding normal tissues (only intra-hybridisation pairs should be considered). Note also that for APOBEC1 hybridisation of stomach samples the opposite may be the case.

REFERENCES

1. Muramatsu, M., Sankaranand, V. S., Anant, S., Sugai, M., Kinoshita, K, Davidson, N. O. & Honjo, T. Specific expression of activation-induced cytidine deaminase (AID), a novel member of the RNA-editing deaminase fully in germinal center B cells. *J. Biol. Chem.* 274, 18470-1476 (1999).
2. Muramatsu M, Kinoshita, K., Fagarasan, S., Yamada, S., Shinkai, Y. & Honjo T. Class switch recombination and hypermutation require activation-induced cytidine deaminase (AID), a potential RNA editing enzyme. *Cell* 102, 553-563 (2000).
3. Revy, P., Muto, T., Levy, Y., Geissmann, F., Plebani, A., Sanal, O. et al. Activation-induced cytidine deaminase (AID) deficiency causes the autosomal recessive form of the Hyper-IgM syndrome (HIGM2). *Cell* 102, 565-575 (2000).
4. Arakawa, H., Hauschild, J. & Buerstedde, J. M. Requirement of the Activation-Induced Deaminase (AID) gene for immunoglobulin gene conversion. *Science* 295, 1301-1306 (2002).
5. Harris, R. S., Sale, J. E., Petersen-Mahrt, S. K. & Neuberger, M. S. AID is essential for immunoglobulin V gene conversion in a cultured B cell line. *Curr. Biol.* 12, 435-438 (2002).
6. Martin, A., Bardwell, P. D., Woo, C. V. J., Fan, A, Shulman, M. J. & Scharff, M. D. Activation-induced cytidine deaminase turns on somatic hypermutation in hybridomas. *Nature* 415, 802-806 (2002).
7. Okazaki, L, Kinoshita, K., Muramatsu, M., Yoshikawa, K., & Honjo T. The AID enzyme induces class switch recombination in fibroblasts. *Nature* 416, 340-345 (2002).
8. Maizels, N. Somatic hypermutation: how many mechanisms diversify V region sequences? *Cell* 83, 9-12 (1995).
9. Weill, J. C. & Reynaud, C. A. Rearrangement/hypermutation/gene conversion: when, where and why? *Immunol Today* 17, 92-97 (1996).
10. Sale, L. E., Calandrini, D. M., Takata, M., Takeda, S. & Neuberger, M. S. Ablation of XRCC2/3 transforms immunoglobulin V gene conversion into somatic hypermutation. *Nature* 412, 921-926 (2001).
11. Ehrenstein, M. R. & Neuberger, M. S. Deficiency in Msh2 affects the efficiency and local sequence specificity of immunoglobulin class-switch recombination: parallels with somatic hypermutation. *EMBO J.* 18, 3484-3490 (1999).
12. Rada, C., Ehrenstein M. R., Neuberger, M. S. & Milstein, C. Hot spot focusing of somatic hypermutation in MSH2-deficient mice suggests two stages of mutational targeting. *Immunity* 9, 135-141 (1998).
13. Wiesendanger, M., Kneitz, B., Edelmann, W., & Scharff, M. D. Somatic hypermutation in MutS homologue (MSH) 3-, MSH6-, and MSH3/MSH6-deficient mice reveals a role for the MSH2-MSH6 heterodimer in modulating the base substitution pattern J. Exp. Med. 191, 579-584 (2000).
14. Lindahl T. Suppression of spontaneous mutagenesis in human cells by DNA base excision-repair. *Mutat. Res.* 462, 129-135 (2000).
15. Sale, J. E. & Neuberger, M. S. TdT-accessible breaks are scattered over the immunoglobulin V domain in a constitutively hypermutating B cell line. *Immunity* 9, 859-869 (1998).
16. Manis, J. P., Tian, M. & Alt, F. W. Mechanism and control of class-switch recombination. *Trends Immunol.* 23, 31-39 (2002).
17. Petersen S., Casellas R., Reina-San-Martin, B., Chen, H. T., Difilippantonio, M, J, et al. AID is required to initiate Nbs1/gamma-H2AX focus formation and mutations at sites of class switching. *Nature* 414, 660-665 (2001).
18. Chen, X., Kinoshita, K. & Honjo, T. Variable deletion and duplication at recombination junction ends: implication for staggered double-strand cleavage in class-switch recombination. *Proc. Natl. Acad. Sci. USA.* 98, 13860-13865 (2001).
19. Sung, J., Bennett, S. E. & Mosbaugh, D. W. Fidelity of uracil-initiated base excision DNA repair in *Escherichia coli* cell extracts. *J. Biol. Chem.* 276, 2276-2285 (2001).
20. Mokkapati, S. K., Fernandez de Henestrosa, A. R., Bhagwat, A. S. *Escherichia coli* DNA glycosylase Mug: a growth-regulated enzyme required for mutation avoidance in stationary-phase cells. *Mol. Microbiol.* 41, 1101-1111 (2001).
21. Schouten, K. A. & Weiss, B. Endonuclease V protects *Escherichia coli* against specific mutations caused by nitrous acid. *Mut. Res.* 435, 245-254 (1999).
22. He, B., Qing, H. & Kow, Y. W. Deoxyxanthosine in DNA is repaired by *Escherichia coli* endonuclease V. Mut. Res. 459, 109-114 (2000).
23. Betz, A. G., Milstein, C., Gonzalez-Fernandez, A, Pannell, R, Larson, T., Neuberger, M. S. Elements regulating somatic hypermutation of an immunoglobulin kappa gene: critical role for the intron enhancer/matrix attachment region. *Cell* 77, 239-248 (1994).
24. Jarmuz A., Chester A., Bayliss J., Gisbourne J., Dunham L, et al. An Anthropoid-Specific Locus of Orphan C to U RNA-Editing Enzymes on Chromosome 22. *Genomics* 79, 285-296 (2002).
25. Yamanaka, S., Balestra, M. E., Ferrell, L. D., Fan, J., Arnold, et al. Apolipoprotein B mRNA-editing protein induces hepatocellular carcinoma and dysplasia in transgenic animals. *Proc, Natl. Acad Sci. USA.* 92, 8483-8487 (1995).
26. Shen, J.-C., Rideout, W. M. & Jones, P. A. High frequency mutagenesis by a DNA methyltransferase. *Cell* 71, 1073-1080 (1992).
27. Navaratnam, N., Fujino, T., Bayliss, J., Jarmuz, A., How, et al. *Escherichia coli* cytidine deaminase provides a molecular model for ApoB RNA editing and a mechanism for RNA substrate recognition. *J. Mol. Biol.* 275, 695-714 (1998).
28. Selker, E. U. Premeiotic instability of repeated sequences in *Neurospora crassa*. *Ann. Rev. Genet.* 24, 579-613 (1990).
29. Jin, D. J. & Zhou, Y. N. Mutational Analysis of structure-function relationship of RNA polymerase in *Escherichia coli*. *Methods Enzymol.* 273, 300-319 (1996).
30. Jarmuz et al. Genomics 79, 285 (2002).

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for preparing a mutant immunoglobulin, which method comprises:
   expressing in a prokaryotic cell a transgene comprising a nucleic acid encoding an immunoglobulin having a functional activity, wherein
   (i) the prokaryotic cell expresses AID mutation activity,
   (ii) expression of AID mutation activity in the prokaryotic cell induces a mutation in the nucleic acid encoding the immunoglobulin, and
   (iii) expression of the mutated nucleic acid produces a mutant immunoglobulin having a modulated functional activity as compared to the immunoglobulin prior to mutation.

2. The method of claim 1, wherein the nucleic acid encoding the immunoglobulin is operably linked to the second half of a specific binding pair.

3. The method of claim 1, wherein said transgene is expressed via an expression vector comprising said nucleic acid encoding said immunoglobulin.

4. The method of claim 3, wherein said expression vector comprises an inducible promoter.

5. The method of claim 1, wherein said transgene has undergone chromosomal integration into the genome of the prokaryotic cell.

6. The method of claim 5, wherein said chromosomal integration is via homologous recombination.

7. The method of claim 3, wherein said expression vector further comprises control sequences which direct hypermutation in said nucleic acid encoding said immunoglobulin.

8. The method of claim 1, wherein the genetic background of the prokaryotic cell confers a UDG deficiency on the prokaryotic cell.

9. The method of claim 1, wherein AID mutation activity is mediated by a homologue selected from Apobec-1, Apobec3C or Apobec3G.

10. The method of claim 1, which is successively repeated.

11. The method of claim 1, wherein AID mutation activity is transiently expressed.

12. The method of claim 1, wherein AID mutation activity is stably expressed.

13. The method of claim 1, wherein said prokaryotic cell is a bacterial cell.

14. The method of claim 13, wherein said bacterial cell is bacteria *E. coli*.

15. The method of claim 1, which further comprises maintaining the prokaryotic cell in a selectable medium to determine whether the prokaryotic cell produces a mutant immunoglobulin having a modulated functional activity as compared to the immunoglobulin prior to mutation.

16. The method of claim 1, which further comprises using binding to magnetic beads to determine whether the prokaryotic cell produces a mutant immunoglobulin having a modulated functional activity as compared to the immunoglobulin prior to mutation.

17. The method of claim 1, which further comprises using affinity chromatography to determine whether the prokaryotic cell produces a mutant immunoglobulin having a modulated functional activity as compared to the immunoglobulin prior to mutation.

18. The method of claim 1, wherein the functional activity is binding affinity for a ligand.

19. The method of claim 18, wherein the ligand is an antigen.

20. The method of claim 1, wherein the functional activity is enzymatic activity.

21. The method of claim 1, wherein the prokaryotic cell is modified to express a fusion protein comprising AID activity operably linked to one half of a specific binding pair having a mutator phenotype.

22. The method of claim 21, wherein the specific binding pair is a DNA binding domain.

* * * * *

SEQUENCE LISTING

```
<160> NUMBER OF SEQ ID NOS: 27

<210> SEQ ID NO 1
<211> LENGTH: 31
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (1)..(3)
<223> OTHER INFORMATION: "n" is any single nucleotide

<400> SEQUENCE: 1
nnngaattca aggctgaaca tgaatccaca g                              31

<210> SEQ ID NO 2
<211> LENGTH: 30
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (1)..(5)
<223> OTHER INFORMATION: "n" is any single nucleotide

<400> SEQUENCE: 2
nnnnngtcga cggagacccc tcactggaga                                30

<210> SEQ ID NO 3
<211> LENGTH: 31
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (1)..(3)
<223> OTHER INFORMATION: "n" is any single nucleotide

<400> SEQUENCE: 3
nnngaattca aggatgaagc ctcacttcag a                              31

<210> SEQ ID NO 4
<211> LENGTH: 30
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (1)..(2)
<223> OTHER INFORMATION: "n" is any single nucleotide
```

```
<400> SEQUENCE: 4
nngactgcag cccatccttc agttttcctg                                          30

<210> SEQ ID NO 5
<211> LENGTH: 34
<212> TYPE: DNA
<213> ORGANISM: artificial sequence
<220> FEATURE:
<223> OTHER INFORMATION: PCR primer for mutagenesis

<400> SEQUENCE: 5
accaacaaac acgttgcagt caatttcata gaaa                                     34

<210> SEQ ID NO 6
<211> LENGTH: 34
<212> TYPE: DNA
<213> ORGANISM: artificial sequence
<220> FEATURE:
<223> OTHER INFORMATION: PCR primer for mutagenesis

<400> SEQUENCE: 6
tttctatgaa attgactgca acgtgtttgt tggt                                     34

<210> SEQ ID NO 7
<211> LENGTH: 33
<212> TYPE: DNA
<213> ORGANISM: Artificial sequence
<220> FEATURE:
<223> OTHER INFORMATION: PCR primer for mutagenesis

<400> SEQUENCE: 7
acctggttcc tgtcctcgag tccctgtggg gag                                      33

<210> SEQ ID NO 8
<211> LENGTH: 33
<212> TYPE: DNA
<213> ORGANISM: Artificial sequence
<220> FEATURE:
<223> OTHER INFORMATION: PCR primer for mutagenesis

<400> SEQUENCE: 8
ctccccacag ggactcgagg acaggaacca ggt                                      33

<210> SEQ ID NO 9
<211> LENGTH: 33
<212> TYPE: DNA
<213> ORGANISM: Artificial sequence
<220> FEATURE:
<223> OTHER INFORMATION: PCR primer for mutagenesis

<400> SEQUENCE: 9
ctgtcctgga gtcccgctgg ggagtgctcc agg                                      33

<210> SEQ ID NO 10
<211> LENGTH: 33
<212> TYPE: DNA
<213> ORGANISM: Artificial sequence
<220> FEATURE:
<223> OTHER INFORMATION: PCR primer for mutagenesis

<400> SEQUENCE: 10
cctggagcac tccccagcgg gactccagga cag                                      33

<210> SEQ ID NO 11
```

<211> LENGTH: 21
<212> TYPE: DNA
<213> ORGANISM: Artificial sequence
<220> FEATURE:
<223> OTHER INFORMATION: PCR primer

<400> SEQUENCE: 11
ttggcgaaat ggcggaaaac c                                             21

<210> SEQ ID NO 12
<211> LENGTH: 22
<212> TYPE: DNA
<213> ORGANISM: Artificial sequence
<220> FEATURE:
<223> OTHER INFORMATION: PCR primer

<400> SEQUENCE: 12
caccgacgga taccacctgc tg                                            22

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
gcgcggctgt gttataattt                                               20

<210> SEQ ID NO 14
<211> LENGTH: 21
<212> TYPE: DNA
<213> ORGANISM: Artificial sequence
<220> FEATURE:
<223> OTHER INFORMATION: PCR primer

<400> SEQUENCE: 14
ttccgtgccg tcatagttat c                                             21

<210> SEQ ID NO 15
<211> LENGTH: 24
<212> TYPE: PRT
<213> ORGANISM: artificial sequence
<220> FEATURE:
<223> OTHER INFORMATION: Synthetic N-terminal fusion sequence

<400> SEQUENCE: 15

Met His His His His His His His Tyr Asp Ile Pro Thr Ala Ser
1               5                   10                  15

Glu Asn Leu Tyr Phe Gln Gly Ser
            20

<210> SEQ ID NO 16
<211> LENGTH: 40
<212> TYPE: DNA
<213> ORGANISM: Artificial sequence
<220> FEATURE:
<223> OTHER INFORMATION: oligodeoxyribonucleotide

<400> SEQUENCE: 16
attattatta ttagctattt atttatttat ttatttattt                         40

<210> SEQ ID NO 17
<211> LENGTH: 42
<212> TYPE: DNA
<213> ORGANISM: Artificial sequence

```
<220> FEATURE:
<223> OTHER INFORMATION: oligodeoxyribonucleotide

<400> SEQUENCE: 17
attattatta ttccgcggat ttatttattt atttatttat tt                    42

<210> SEQ ID NO 18
<211> LENGTH: 40
<212> TYPE: DNA
<213> ORGANISM: Artificial sequence
<220> FEATURE:
<223> OTHER INFORMATION: oligodeoxyribonucleotide

<400> SEQUENCE: 18
attattgtta ttatcaattt gtttatttgt ttatttattt                       40

<210> SEQ ID NO 19
<211> LENGTH: 40
<212> TYPE: DNA
<213> ORGANISM: Artificial sequence
<220> FEATURE:
<223> OTHER INFORMATION: oligodeoxyribonucleotide

<400> SEQUENCE: 19
attattgtta ttatcgattt gtttatttgt ttatttattt                       40

<210> SEQ ID NO 20
<211> LENGTH: 40
<212> TYPE: DNA
<213> ORGANISM: Artificial sequence
<220> FEATURE:
<223> OTHER INFORMATION: oligodeoxyribonucleotide

<400> SEQUENCE: 20
attattgtta ttaactattt gtttatttgt ttatttattt                       40

<210> SEQ ID NO 21
<211> LENGTH: 42
<212> TYPE: DNA
<213> ORGANISM: Artificial sequence
<220> FEATURE:
<223> OTHER INFORMATION: oligodeoxyribonucleotide

<400> SEQUENCE: 21
aaataaataa ataaataaat aaatccgcgg aataataata at                    42

<210> SEQ ID NO 22
<211> LENGTH: 26
<212> TYPE: DNA
<213> ORGANISM: Artificial sequence
<220> FEATURE:
<223> OTHER INFORMATION: oligodeoxyribonucleotide

<400> SEQUENCE: 22
gttctggcaa atattctgaa atgagc                                      26

<210> SEQ ID NO 23
<211> LENGTH: 209
<212> TYPE: DNA
<213> ORGANISM: artificial sequence
<220> FEATURE:
<223> OTHER INFORMATION: RpoB vector DNA - see figure 3

<400> SEQUENCE: 23
ggttccagcc agctgtctca gtttatggac cagaacaacc cgctgtctga gattacgcac    60
```

```
aaacgtcgta tctccgcact cggcccaggc ggtctgaccc gtgaacgtgc aggcttcgaa      120
gttcgagacg tacacccgac tcactacggt cgcgtatgtc caatcgaaac ccctgaaggt      180
ccgaacatcg gtctgatcaa ctctctctg                                        209

<210> SEQ ID NO 24
<211> LENGTH: 66
<212> TYPE: PRT
<213> ORGANISM: artificial sequence
<220> FEATURE:
<223> OTHER INFORMATION: RpoB protein sequence - figure 3

<400> SEQUENCE: 24

Ser Gln Leu Ser Gln Phe Met Asp Gln Asn Asn Pro Leu Ser Glu Ile
1               5                   10                  15

Thr His Lys Arg Arg Ile Ser Ala Leu Gly Pro Gly Gly Leu Thr Arg
            20                  25                  30

Glu Arg Ala Gly Phe Glu Val Arg Asp Val His Pro Thr His Tyr Gly
        35                  40                  45

Arg Val Cys Pro Ile Glu Thr Pro Glu Gly Pro Asn Ile Gly Leu Ile
    50                  55                  60

Asn Ser
65

<210> SEQ ID NO 25
<211> LENGTH: 24
<212> TYPE: DNA
<213> ORGANISM: artificial sequence
<220> FEATURE:
<223> OTHER INFORMATION: gyrA vector DNA sequence -figure 4

<400> SEQUENCE: 25
ggtgactcgg cggtctatga cacg                                             24

<210> SEQ ID NO 26
<211> LENGTH: 8
<212> TYPE: PRT
<213> ORGANISM: Artificial sequence
<220> FEATURE:
<223> OTHER INFORMATION: GyrA Protein sequence- figure 4

<400> SEQUENCE: 26

Gly Asp Ser Ala Val Tyr Asp Thr
1               5

<210> SEQ ID NO 27
<211> LENGTH: 209
<212> TYPE: DNA
<213> ORGANISM: Artificial sequence
<220> FEATURE:
<223> OTHER INFORMATION: RpoB vector for Apobec - figure 6

<400> SEQUENCE: 27
ggttccagcc agctgtctca gtttatggac cagaacaacc cgctgtctga gattacgcac      60
aaacgtcgta tctccgcact cggcccaggc ggtctgaccc gtgaacgtgc aggcttcgaa      120
gttcgagacg tacacccgac tcactacggt cgcgtatgtc caatcgaaac ccctgaaggt      180
ccgaacatcg gtctgatcaa ctctctctg                                        209
```